United States Patent [19]

Raeymaekers et al.

[11] 4,179,505

[45] Dec. 18, 1979

[54] 5-[4-(DIARYLMETHYL)-1-PIPERAZINYLALKYL]BENZIMIDAZOLE DERIVATIVES

[75] Inventors: Alfons H. M. Raeymaekers, Beerse; Josephus L. H. Van Gelder, Tielen; Gustaaf M. Boeckx, Oud-Turnhout; Lodewijk L. Van Hemeldonck, Rijkevorsel, all of Belgium

[73] Assignee: Janssen Pharmaceutica N.V., Beerse, Belgium

[21] Appl. No.: 866,882

[22] Filed: Jan. 4, 1978

Related U.S. Application Data

[63] Continuation-in-part of Ser. No. 782,651, Mar. 30, 1977, abandoned.

[51] Int. Cl.$^2$ .................. A61K 31/495; C07D 401/14; C07D 403/06; C07D 409/14

[52] U.S. Cl. ........................... 424/250; 424/232; 544/360; 544/364; 544/370; 544/374; 544/396; 548/305; 548/306; 548/325; 548/327; 548/329; 548/330; 548/334

[58] Field of Search ............... 544/370, 364; 424/250, 424/232

[56] References Cited

U.S. PATENT DOCUMENTS

| 3,133,069 | 5/1964 | Ash et al. | 544/370 |
| 3,362,956 | 1/1968 | Archer | 544/370 |
| 3,491,098 | 1/1970 | Archer | 544/370 |

*Primary Examiner*—Alton D. Rollins
*Attorney, Agent, or Firm*—Salvatore R. Conte

[57] ABSTRACT

Novel 5-[4-(diarylmethyl)-1-piperazinylalkyl]benzimidazole derivatives having antiallergic and antihistaminic properties.

39 Claims, No Drawings

5-[4-(DIARYLMETHYL)-1-PIPERAZINYLALKYL]-BENZIMIDAZOLE DERIVATIVES

CROSS-REFERENCE TO RELATED APPLICATIONS

This is a continuation-in-part of our copending application Ser. No. 782,651, filed Mar. 30, 1977 and now abandoned.

BACKGROUND OF THE INVENTION

In U.S. Pat. Nos. 3,362,956 and 3,472,854 there are described a number of 1-(heterocyclylalkyl)piperazines having depressant activities on the autonomous nervous system, the cardiovascular system and the skeletal muscular system. The compounds of this invention differ from such known compounds essentially by the nature of the benzimidazole group or the position where the piperazinylmethyl moiety is substituted thereon.

DESCRIPTION OF THE PREFERRED EMBODIMENTS

This invention relates to novel 5-[4-(diarylmethyl)-1-piperazinylalkyl]benzimidazole derivatives which may structurally be represented by the formula:

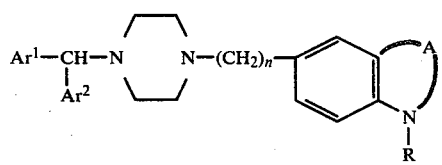
(I)

and the pharmaceutically acceptable acid addition salts thereof, wherein:

$Ar^1$ and $Ar^2$ are each independently selected from the group consisting of phenyl, halophenyl, (lower alkyl)phenyl, (lower alkyloxy)phenyl, nitrophenyl, thienyl and pyridinyl;

R is a member selected from the group consisting of hydrogen, lower alkyl, aryl(lower alkyl), hydroxy(lower alkyl), cycloalkyl, (lower alkyl)carbonyloxy(lower alkyl), aroyloxy(lower alkyl), (lower alkyl)sulfonyloxy(lower alkyl), halo(lower alkyl), arylthio(lower alkyl) and (lower alkyl)oxy(lower alkyl) wherein said aryl is selected from the group consisting of phenyl, substituted phenyl, thienyl and pyridinyl, said substituted phenyl being phenyl having from 1 to 2 substituents independently selected from the group consisting of halo, lower alkyl, and lower alkyloxy;

A is a member selected from the group consisting of the bivalent radicals —NH—CO— and —N=C($R^1$)—, said bivalent radicals being attached to the benzene nucleus with their nitrogen atom, and, said $R^1$ being selected from the group consisting of hydrogen, lower alkyl, aryl(lower alkyl), hydroxy(lower alkyl), cycloalkyl, aryl, amino, (lower alkyl)carbonylamino, (lower alkyl)carbonyloxy(lower alkyl), aroyloxy(lower alkyl), (lower alkyl)oxycarbonylamino, (lower alkyl)aminocarbonylamino, and (lower alkyl)oxycarbonyl(lower alkyl), wherein said aryl is selected from the group consisting of phenyl, substituted phenyl, pyridinyl, furanyl, thienyl and halothienyl, said substituted phenyl having from 1 to 2 substituents independently selected from the group consisting of halo, lower alkyl and lower alkyloxy; and n is an integer of from 1 to 2 inclusive, provided that when said n is 2 then said R is selected from the group consisting of hydrogen, lower alkyl and cycloalkyl, and then said $R^1$ is selected from the group consisting of hydrogen, lower alkyl, cycloalkyl and aryl.

As used in the foregoing and in following definitions, "lower alkyl" is meant to include straight and branch chained hydrocarbon radicals having from 1 to 6 carbon atoms, such as, for example, methyl, ethyl, 1-methylethyl, propyl, 1-methylpropyl, 2-methylpropyl, butyl, pentyl, hexyl and the like; "cycloalkyl" refers to cyclic hydrocarbon radicals having from 3 to 6 carbon atoms such as, cyclopropyl, cyclobutyl, cyclopentyl and cyclohexyl; and the term "halo" refers to halogens of atomic weight less than 127, i.e., fluoro, chloro, bromo and iodo.

The compounds of formula (I) wherein n is 1, (I'), can generally be prepared starting from an appropriate benzenediamine of the formula:

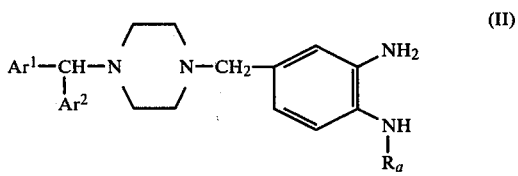
(II)

wherein $Ar^1$ and $Ar^2$ are as previously defined and $R_a$ is selected from the group consisting of hydrogen, lower alkyl, aryl(lower alkyl), hydroxy(lower alkyl), cycloalkyl and (lower alkyl)oxy(lower alkyl) by subjecting the latter to a cyclisation reaction with an appropriate cyclizing agent and, optionally, further modifying the R and $R^1$ substituents in the thus obtained compounds of formula (I') following art-known procedures.

Compounds of formula (I') which may be prepared directly by cyclizing a benzenediamine of formula (II) are those of the formula

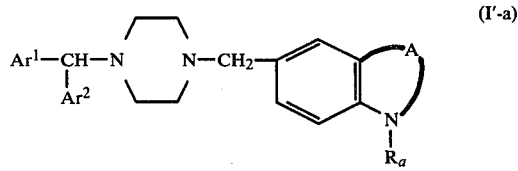
(I'-a)

wherein $Ar^1$, $Ar^2$ and $R_a$ are as previously defined and wherein $A^1$ represents a radical of the formula —NH—C(O)— or a radical of the formula —N=C($R_a^1$)— wherein said $R_a^1$ is selected from the group consisting of hydrogen, lower alkyl, aryl(lower alkyl), hydroxy(lower alkyl), cycloalkyl, aryl, amino, (lower alkyl)carbonylamino, (lower alkyl)carbonyloxy(lower alkyl), (lower alkyl)oxycarbonylamino, (lower alkyl)oxycarbonyl(lower alkyl), and aroyloxy(lower alkyl).

The cyclisation reactions of 1,2-benzenediamines to obtain benzimidazoles and benzimidazol-2-ones are generally known and they may all be carried out under such conditions as are described in the literature for the preparation of known benzimidazoles and benzimidazol-2-ones starting from the corresponding benzenediamines. Depending on the nature of $A^1$ in the compounds (I'-a) to be prepared, the following cyclizing agents may, for example, be utilized.

In the preparation of compounds of formula (I'-a) wherein A¹ is the radical —NH—C(O)—, said compounds being represented by the formula:

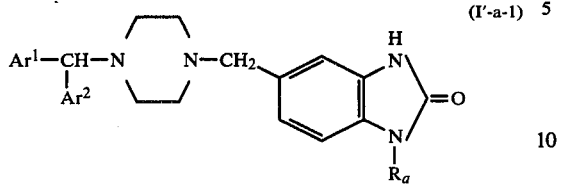

there may be used urea, carbonyl dichloride or an alkali metal isocyanate as a cyclizing agent. Good results have been obtained with urea, in which case the compounds (I'-a-1) are conveniently obtained by stirring and heating the reactants together in the absence of any solvent.

In the preparation of compounds of formula (I'-a) wherein A¹ is a radical of the formula —N=C($R_a^1$)—, said compounds being represented by the formula:

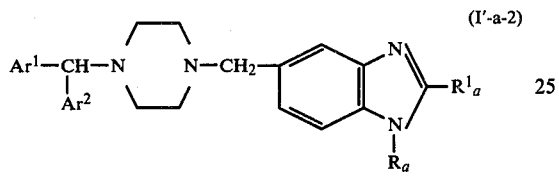

the nature of the cyclizing agent to be used further depends on the nature of $R_a^1$ in said formula (I'-a-2).

When $R_a^1$ represents hydrogen there may be used formic acid or an appropriate 1,1',1''-[methylidynetris(oxy)]tris(lower alkane). In a preferred method the cyclisation is accomplished by stirring and heating a mixture of (II) and 1,1',1''-[methylidynetris(oxy)]trisethane in acetic acid.

When $R_a^1$ represents lower alkyl, aryl(lower alkyl), hydroxy(lower alkyl), cycloalkyl or aryl, one may advantageously use a carboxylic acid of the formula

R²—COOH    (III)

wherein R² is lower alkyl, aryl(lower alkyl), hydroxy(lower alkyl), cycloalkyl or aryl; or a functional derivative of such acid, such as, for example, an acyl halide, an ester, an amide or a nitrile, or and iminoester of the formula HN=C(R²)—O—(lower alkyl)    (IV)

wherein R² is as defined hereabove; or an aldehyde of the formula:

or an addition product thereof with an alkali metal hydrogen sulfite. When the cyclizing agent is an aldehyde there may be added to the reaction mixture an appropriate oxidizing agent such as, for example, nitrobenzene, mercuric oxide, Cu(II) and Pb(II) salts or other suitable oxidants as known in the art, or the aldehyde itself, when added in excess, may serve as an oxidant. In a preferred method of conducting the above cyclisation reaction there is used an iminoester of formula (IV) and the desired compounds (I'-a-2) are then easily prepared by stirring the reactants together first some time at room temperature and thereafter at an elevated temperature in an acidic medium, such as, for example, acetic acid, or a lower alkanol, whereto an appropriate acid, e.g., hydrochloric acid has been added. When the iminoester (IV) is in the form of an acid addition salt there is no need for adding additional acid.

When $R_a^1$ is an amino group, ring closure may be accomplished with cyanamide, or a metal salt thereof, preferably an alkali or earth alkali metal salt, or with BrCN. Ring closure with cyanamide may be carried out by stirring an heating the substituted benzenediamine together with cyanamide in the presence of an appropriate nonoxydizing acid, such as, for example, hydrochloric, hydrobromic, sulfuric, phosphoric, acetic and the like acids. The reaction is preferably carried out in aqueous medium although mixtures of water with reaction-inert organic solvents such as, for example, halogenated alifatic and aromatic hydrocarbons, e.g. dichloromethane; trichloromethane, 1,2-dichloroethane, chlorobenzene etc. may advantageously be employed, especially when an organic acid is used. Conveniently the benzenediamine is first converted into an acid addition salt and then reacted with cyanamide. When metal cyanamides are used as cyclizing agents an excess of the acid is added to liberate the free cyanamide from the salt. Ring closure with BrCN is advantageously conducted in aqueous medium and at room temperature. The benzenediamine is preferably used in the form of a dihydrochloride or other salt.

When $R_a^1$ represents (lower alkyl)carbonylamino, (lower alkyl)carbonyloxy(lower alkyl), aroyloxy(lower alkyl), (lower alkyl)oxycarbonylamino or (lower alkyl)oxycarbonyl(lower alkyl) there may be used as a cyclizing agent a compound of the formula:

wherein R³ is (lower alkyl)carbonylamino, (lower alkyl)carbonyloxy(lower alkyl), aroyloxy(lower alkyl), (lower alkyl)oxycarbonylamino or (lower alkyl)oxycarbonyl(lower alkyl) and the reaction may be carried out by stirring and heating the reactants together in the presence of an appropriate acid, preferably a (lower alkyl)carboxylic acid such as acetic, propanoic and the like acids. When R³ in formula (VI) represents a (lower alkyl)carbonylamino group the foregoing reaction is preferably conducted in an appropriate organic solvent, e.g., a halogenated hydrocarbon such as dichloromethane, trichloromethane and the like.

When $R_a^1$ represents a (lower alkyl)oxycarbonylamino group there may also be used as a cyclizing agent a compound of the formula:

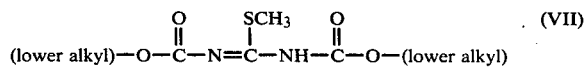

and the cyclisation reaction is carried out in a manner similar to that described hereinabove for the preparation of compounds (I'-a-2) wherein $R_a^1$ represents (lower alkyl)carbonylamino or (lower alkyl)oxycarbonylamino.

Some of the compounds of the formulae (I'-a-1) and (I'-a-2) can optionally be converted into other compounds of formula (I') by modification and substitution of the $R_a$ and $R_a^1$ groups according to art-known procedures such as the following:

Compounds of formula (I') wherein $R^1$ represents an amino group can also be derived from a corresponding compound wherein $R^1$ represents a (lower alkyl)oxycarbonylamino group by decarboxylating the latter in the usual manner, e.g. by the treatment thereof with aqueous alkali.

Compounds of formula (I') wherein $R^1$ represents a (lower alkyl) aminocarbonylamino group are easily derived from a corresponding compound wherein $R^1$ represents amino by stirring and heating the latter with an appropriate isocyanato(lower alkane) in an appropriate reaction-inert organic solvent such as, for example, tetrahydrofuran.

Compounds of formula (I') wherein R and/or $R^1$ represent a (lower alkyl)carbonyloxy(lower alkyl)-group or an aroyloxy(lower alkyl)group can be prepared by subjecting a corresponding hydroxy(lower alkyl) substituted compound to an O-acylation reaction with an appropriate acylating agent derived from respectively an appropriate (lower alkyl)carboxylic acid or arylcarboxylic acid, preferably an acyl halide, such as the chloride, or, an anhydride derived from such acid. The acylation reactions may be carried out following standard procedures as generally known in the art.

Compounds of formula (I') wherein R and/or $R^1$ represent a hydroxy(lower alkyl) chain can in turn be derived from their esters with e.g. a lower alkyl- or arylcarboxylic acid by subjecting the latter to alkaline hydrolysis.

In a similar manner there may be prepared compounds (I') wherein R represents (lower alkyl)sulfonyloxy(lower alkyl) by the reaction of the corresponding alcohol with an appropriate (lower alkane)sulfonyl chloride.

Compounds of formula (I') wherein R represents halo(lower alkyl) can also be derived from the corresponding compounds wherein R represents hydroxy(lower alkyl) by halogenating the latter with an appropriate halogenating agent as generally known in the art, such as, for example, thionyl chloride, sulfuryl chloride, phosphor pentachloride, phosphor pentabromide, phosphoryl chloride and the like. Iodides are preferably derived from the corresponding chloride or bromide by the replacement of that halogen with iodine.

Compounds of formula (I') wherein R represents arylthio(lower alkyl) are conveniently prepared by the reaction of an appropriate reactive ester derived from the corresponding hydroxy(lower alkyl)substituted compound with an appropriate alkali metal arenethiolate, preferably the sodium salt, in an appropriate reaction-inert medium such as, for example a mixture of a lower alkanol, e.g. methanol or ethanol and a relatively polar organic solvent such as N,N-dimethylformamide, N,N-dimethylacetamide, hexamethylphosphoric triamide, dimethylsulfoxide and the like. Suitable reactive esters that may by employed therefor include halides and sulfonate esters such as methanesulfonates and 4-methylbenzenesulfonates. The preparation of halides and methanesulfonates is described hereinabove and other reactive sulfonate esters may be prepared following the procedure described for the preparation of (lower alkyl)sulfonates, using however an appropriate sulfonyl chloride as the sulfonylating agent.

Compounds of the formula (I') wherein A is a radical of the formula $-N=C(NH_2)-$ and R represents lower alkyl, aryl (lower alkyl), cycloalkyl or (lower alkyl)oxy(lower alkyl) said R being represented by $R_b$ and said compounds by the formula (I'-c) can also be prepared by aminating a corresponding compound wherein A represents $-N=CH-$, (I'-b), following the procedure outlined in J. Gen. Chem. U.S.S.R., 33, 2289 (1963), using an appropriate metal amide, preferably sodium amide, and an appropriate organic solvent such as, for example, N,N-dimethylbenzenamine or dimethylbenzene, the former being preferred when R represents alkyl, phenyl(lower alkyl) or (lower alkyl)oxy(lower alkyl), and the latter when R is cycloalkyl.

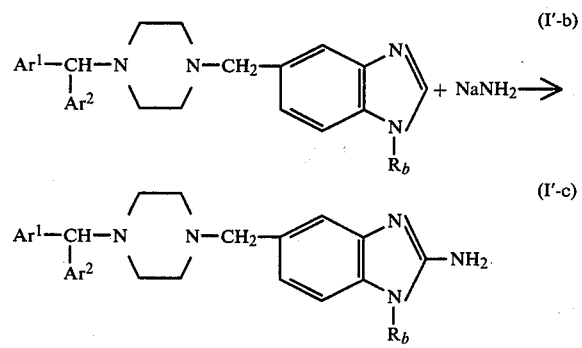

An additional method of preparing compounds of formula (I') wherein R is hydrogen, lower alkyl, aryl(lower alkyl), cycloalkyl or (lower alkyl)oxy(lower alkyl), said R being represented by $R_c$, and wherein A is a radical of the formula $-N=C(R^1)-$ wherein $R^1$ is hydrogen, lower alkyl, aryl(lower alkyl), cycloalkyl, amino, (lower alkyl)carbonylamino, (lower alkyl)carbonyloxy(lower alkyl), aroyloxy(lower alkyl), or aryl, said $R_1$ being represented by $R_c^1$ and said compounds by the formula (I'-d), comprises the reaction of a compound of the formula (VIII) with a compound of the formula (IX). In said formulae (VIII) and (IX), $Ar^1$, $Ar^2$, $R_c$ and $R_c^1$ are as previously defined and either of X and $X^1$ is a 1-piperazinyl group, the other being a reactive ester radical such as, for example, halo, preferably chloro or bromo, or a sulfonyloxy group, preferably methylsulfonyloxy or 4-methylphenylsulfonyloxy.

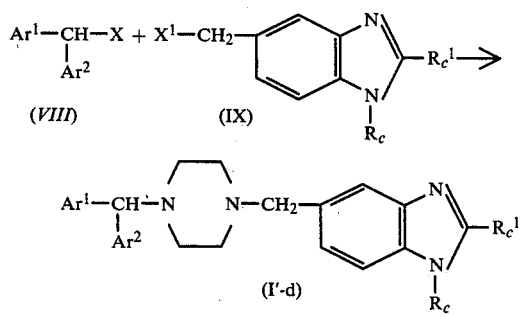

The reaction of (VIII) with (IX) is preferably conducted in an appropriate, reaction-inert organic solvent such as, for example, a lower alkanol, e.g., methanol, ethanol, propanol and the like alkanols, an aromatic hydrocarbon, e.g., benzene, methylbenzene, dimethylbenzene and the like; an ether, e.g., 1,4-dioxane, 2,2'-oxybispropane and the like; a ketone, e.g., 4-methyl-2- pentanone; N,N-dimethylformamide; nitrobenzene and the like. The addition to the reaction mixture of an appropriate base, such as, for example, an alkali or earth alkali metal carbonate or hydrogen carbonate, may be utilized to pick up the acid that is liberated during the course of the reaction. A small amount of an appropriate metal iodide e.g., sodium or potassium iodide, may be added as a reaction promotor. Somewhat elevated temperatures are appropriate to enhance the rate of the reaction and preferably the reaction is carried out at the reflux temperature of the reaction mixture.

The compounds of formula (I) wherein n is 2, (I''), can be prepared by the following sequence of reactions.

An appropriate benzenediamine of the formula (X) wherein $Ar^1$ and $Ar^2$ are as previously defined and $R_d$ is hydrogen, lower alkyl or cycloalkyl is subjected to a cyclisation reaction with an appropriate cyclizing agent following the procedures described hereinabove for the preparation of compounds (I'-a) starting from (II) to obtain an intermediate of formula (XI) wherein $Ar^1$, $Ar^2$ and $R_d$ have the above-defined meaning and $A^2$ is selected from the group consisting of —NH—C(O)— and —N=C($R_d^1$)— wherein $R_d^1$ is hydrogen, lower alkyl, cycloalkyl or aryl. The latter intermediate is then reacted with an appropriate chlorinating agent, preferably thionyl chloride, whereupon there is obtained an intermediate of the formula (XII). The desired compounds (I'') are then conveniently prepared by subjecting (XII) to a reductive dehalogenation reaction, for example, by hydrogenating (XII) in the presence of an appropriate catalyst such as palladium-on-charcoal. In order to avoid side reactions there is preferably added to the reaction mixture a small amount of a suitable catalyst-poison such as, for example thiophene.

The foregoing reactions are illustrated in the following schematic representation.

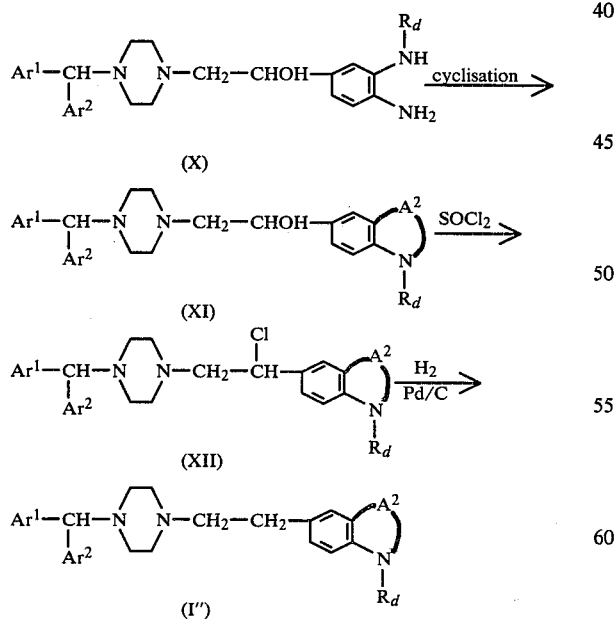

In all of the foregoing and following preparations the reaction products are isolated from the reaction mixture, and, if necessary, further purified according to standard procedures known in the art.

The benzenediamines of formula (II), used as starting materials herein, can generally be prepared by the following sequence of reactions.

An appropriate 1-(diarylmethyl)piperazine of formula (XIII) wherein $Ar^1$ and $Ar^2$ are as previously defined, is reacted with 1-chloro-4-(chloromethyl)-2-nitrobenzene or 4-(chloromethyl)-1-methoxy-2-nitrobenzene by stirring and heating the reactants together, in an appropriate organic solvent, such as, for example, a lower alkanol, e.g., ethanol or propanol to obtain an intermediate of formula (XIV) wherein $R^4$ represents chloro or methoxy. The latter is then reacted with an appropriate amine of the formula (XV) wherein $R_a$ has the previously indicated meaning to yield an intermediate of the formula (XVI). The said reaction can be conducted in an appropriate organic solvent, such as, for example, dimethylsulfoxide, N,N-dimethylformamide, N,N-dimethylacetamide, a lower alkanol, e.g., ethanol and the like, or, when the amine reactant has suitable solvent properties, in the absence of any extraneous solvent. Working at somewhat elevated temperatures is advantageous to enhance the reaction rate.

The desired intermediates of formula (II) are obtained by reducing the intermediate (XVI), obtained in the previous step, following standard nitro-to-amine reduction procedures, such as, for example, by the treatment of (XVI) with nascent hydrogen or, preferably, by catalytic hydrogenation using an appropriate catalyst such as Raneynickel.

The foregoing reaction sequence is more clearly illustrated in the following schematic representation.

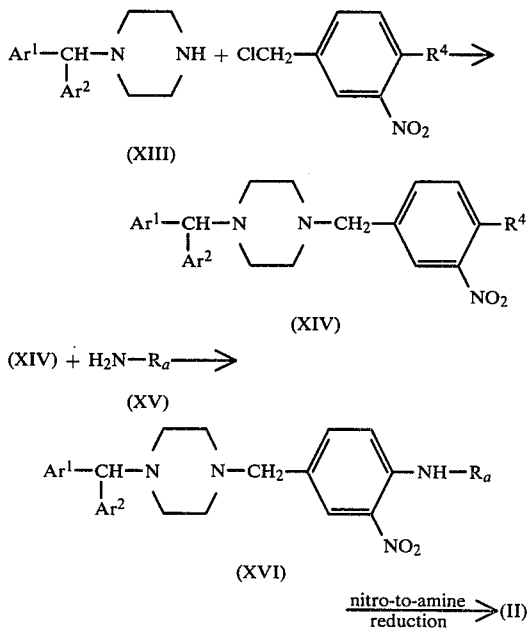

Starting materials of formula (IX) can generally be prepared by the following reaction sequence:

4-Fluoro-3-nitrobenzoic acid is reacted with an appropriate amine of formula (XVII), wherein $R_c$ is as previously defined, in a similar manner as described hereabove for the reaction of (XIV) with (XV). The thus obtained intermediate (XVIII) is then subjected to a nitro-to-amine reduction reaction as previously described, yielding an intermediate of formula (XIX). The latter is then converted into a benzimidazole derivative of formula (XX) by the cyclisation with an appropriate cyclizing agent as previously described for the preparation of compounds (I') starting from (II). The carboxylic acid (XX) is then converted into the corresponding carbonyl chloride (XXI) in the usual manner, e.g., by the reaction with thionyl chloride, and the thus obtained (XXI) is then reacted with an appropriate lower alkanol, (XXII), to obtain a lower alkylester of formula (XXIII). The latter is then reduced to the corresponding alcohol, (XXIV), with an appropriate reducing agent, such as, for example, sodium dihydrobis(2-methoxyethoxy)aluminate (Red-A1). The desired starting materials of formula (IX) wherein $X^1$ represents a reactive ester group, $X_a^1$, said reactive esters being represented by the formula (IX-a), are then conveniently obtained by converting (XXIV) into a reactive ester following standard procedures as known in the art. Halides are generally prepared by the reaction of (XXIV) with an appropriate halogenating agent such as, for example, thionyl chloride, sulfuryl chloride, phosphor pentachloride, phosphor pentabromide, phosphoryl chloride and the like. When the reactive ester is an iodide it is preferably prepared from the corresponding chloride or bromide by the replacement of than halogen with iodine. Other reactive esters such as methanesulfonates and 4-methylbenzenesulfonates are obtained by the reaction of the alcohol with an appropriate sulfonyl halide such as, for example, methanesulfonyl chloride and 4-methylbenzenesulfonyl chloride respectively.

Starting materials of formula (IX) wherein $X^1$ stands for a piperazine moiety, said piperazine derivatives being represented by the formula (IX-b) can be obtained by the reaction of (IX-a) with piperazine following art-known N-alkylating procedures, e.g. as described hereinabove for the preparation of compounds (I'-d) by the reaction of (VIII) with (IX).

The foregoing procedures can be illustrated schematically as follows:

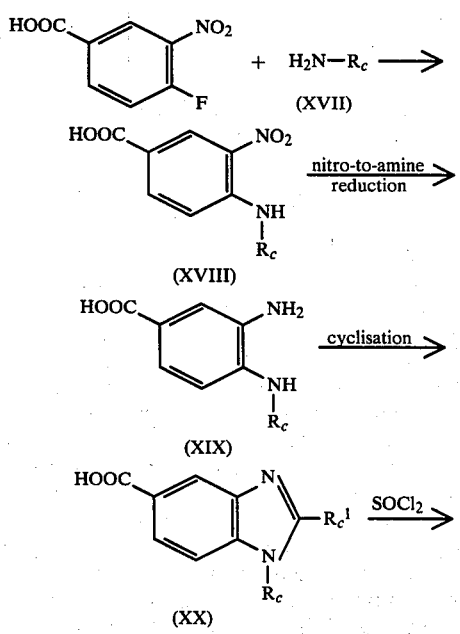

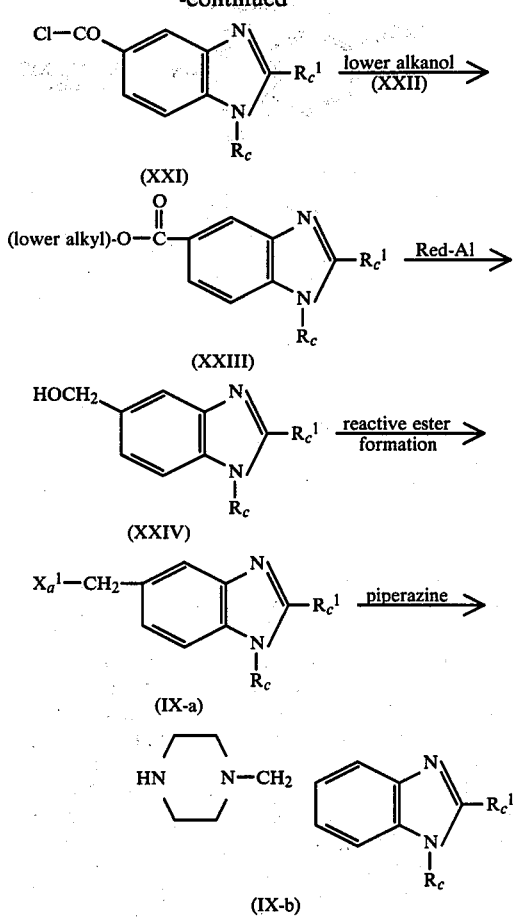

Starting materials of the formulae (IX-a) and (IX-b) wherein $R_c$ stands for hydrogen, (IX-a-1) and (IX-b-1) respectively, can alternatively be prepared starting from 4-amino-3-nitrobenzaldehyde, by carrying out the following steps:

(i) simultaneously reducing the aldehyde and the nitro group by catalytic hydrogenation in the presence of an appropriate catalyst, such as, for example, Raney-nickel to obtain 3,4-diaminobenzenemethanol;

(ii) cyclizing the latter with an appropriate cyclizing agent as previously described to yield a benzimidazolemethanol of formula (XXV);

(iii) converting the latter into a reactive ester of formula (IX-a-1) in the usual manner as described hereabove; and (iv) in order to obtain a piperazine derivative of formula (IX-b-1) reacting (IX-a-1) with piperazine as indicated hereabove.

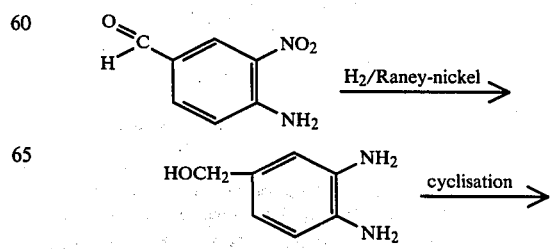

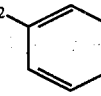

(XXV)

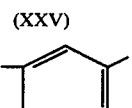

(IX-a-1)

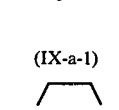

(IX-b-1)

Starting materials of formula (X) can be prepared according to the following reaction sequence:

An appropriate compound of formula VIII wherein X represents a 1-piperazinyl radical, (VIII-a), is first reacted with 2-bromo-1-(4-chloro-3-nitrophenyl)ethanone to obtain an intermediate of formula (XXVI). The ketone group of (XXVI) is then reduced to the corresponding alcohol with an appropriate reducing agent, preferably sodium borohydride. The thus obtained (XXVII) is then reacted with an appropriate amine (XXVIII) wherein $R_d$ is as previously defined following the same procedure as described hereinabove for the preparation of (XVI) starting from (XIV) and (XV) and the nitro group of the thus obtained (XXIX) is then subjected to a standard nitro-to-amine reduction reaction to yield the desired starting materials of formula (X).

The foregoing reactions are illustrated as follows:

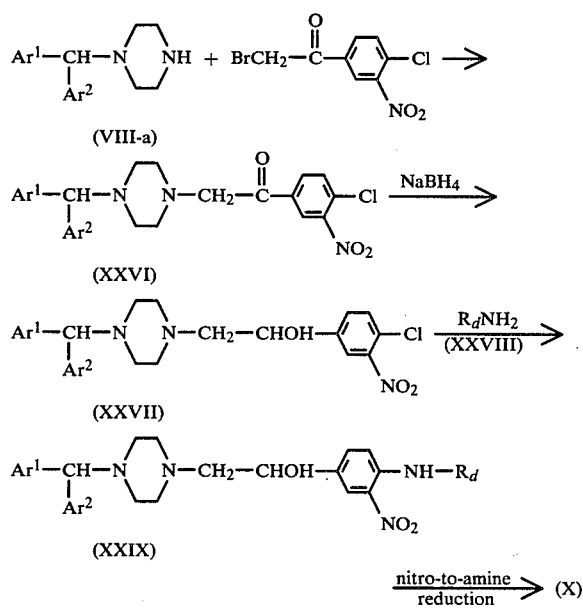

Starting materials and precursors used in all of the preceding procedures for which no specific preparations are given herein, are generally know and/or may all be prepared following art-known methodologies as described in the literature for the preparation of similar known compounds.

The compounds of the formulae (II) and (XVI) are deemed to be novel and as useful intermediates for the preparation of the compounds of formula (I) they constitute an additional feature of this invention.

The compounds of formula (I) may be converted to the therapeutically active non-toxic acid addition salt form by treatment with an appropriate acid, such as, for example, an inorganic acid, such as hydrohalic acid, e.g., hydrochloric, hydrobromic, and the like, and sulfuric acid, nitric acid, phosphoric acid and the like; or an organic acid, such as, for example, acetic, propanoic, hydroxyacetic, 2-hydroxypropanoic, 2-oxopropanoic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, benzoic, 3-phenyl-2-propenoic, α-hydroxybenzeneacetic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. Conversely, the salt form can be converted by treatment with alkali into the free base form.

The compounds of formula (I) and their pharmaceutically acceptable acid addition salts have useful pharmacological activities. More particularly they strongly inhibit at very low doses the action of a number of vasoactive agonists, such as, for example, histamine and serotonine. Such useful pharmacological properties are clearly evidenced by their excellent activity in the following test-procedures.

A. Anti-histamine Activity In "Vitro"

Guinea-pig ileum strips are suspended in a 100 ml Tyrode bath at 37.5° C. with a preload of 0.75 g and gassed with 95% $O_2$ and 5% $CO_2$.

The histamine- (0.5 mg/liter) induced spasms are recorded Kymographically with an isotonic lever giving a 5-fold magnification. The interaction of the compound to be tested (5-minutes incubation time) with the agonist is studied. When tested under these conditions, the compounds of formula (I) and their pharmaceutically acceptable acid addition salts exhibit a 50% inhibition of the histamine-induced spasms at a concentration as low as from 0.0025 to 0.16 mg/ml.

B. Anti-anaphylactic and Antihistaminic Effects In "Vivo"

The anti-anaphylactic and antihistaminic effects of the subject compounds (I) and salts thereof are studied in "vivo" in guinea pigs.

Guinea pigs, weighing between 400 and 500 g, are sensitized to ovalbumin by subplantar (s.p.) injection of 0.05 ml of antiserum in the left hind paw. The animals are then starved and treated orally, 24 hours after the sensitization, with saline (=control animals) or a particular dose of the compound under investigation.

The histamine injection (at a dose of 50 μg) was given s.p. in the right hind paw 2 hours after the oral pretreatment with the compound. The diameters of both hind paws are first measured before the histamine injection is given and again 10 minutes thereafter. The animals are challenged intravenously with 0.6 mg of ovalbumin 30 minutes after the histamine injection. All control animals develop typical primary anaphylactic shock symptoms (coughing, difficult breathing, convulsions) and 85% of these control animals die within 15 minutes after the ovalbumin injection. Protection against death is used as the criterion for possible drug effects.

The median histamine paw oedema in 200 control animals 10 minutes after the histamine injection is 15 units (1 unit = 0.1 mm). Reactions below 10 units occuring in less than 5% of the control animals are defined as effective inhibition of histamine oedema in the compound-treated animals.

The compounds of formula (I) and salts thereof show a 100% activity against anaphylaxis in guinea pigs when given at a single oral dose of 2.5 mg/kg. At the same dose they effectively reduce the histamine-induced paw oedema.

C. Activity Against Passive Cutaneous Anaphylaxis In Rats

Passive cutaneous anaphylaxis in the rat has been studied extensively as a model for immediate hypersensitivity due to "reaginic" antibodies. For this test, serum containing this type of antibody is prepared according to the procedure described in Immunology, 7, 681 (1964) and injected intradermally at two different sites on the back of the test animals. 48 Hours later ovalbumin and tryptan blue are injected intravenously. A score is given independently by two observers to every reaction site on the exposed inner skin by comparison with standard reaction intensities. The highest intensity score for a single reaction site is 4 and the highest total score for a single rat is therefore, 16 (4×2 sites×2 observers). Treatment with the compound to be tested or with water (control animals) is given orally 2 hours before the ovalbumin-injection. The effectiveness of the treatment is evaluated by comparing the intensities of the tryptan blue color at the reaction sites in water-treated and compound-treated rats. Results are expressed as $ED_{50}$-values, i.e., the dose required to produce a 50% inhibition of the induced passive cutaneous anaphylaxis in rats. $ED_{50}$-values determined for compounds of formula (I) and salts thereof were found to be as low as from 0.16 to 5 mg/kg.

As a result of their useful pharmacological properties, the subject compounds (I) and pharmaceutically acceptable acid addition salts thereof are generally found active as antihistaminic, anti-allergic and anti-asthamtic agents in doses ranging from about 0.2 to about 10 mg/kg body weight upon systemic administration to warm-blooded animals.

In view of their useful antihistaminic, anti-allergic and anti-asthmatic activity, the subject compounds may be formulated into various pharmaceutical forms for administration purposes. To prepare the pharmaceutical compositions of this invention, an effective antihistaminic, antianaphylactic or anti-asthmatic amount of the particular compound, in base or acid-addition salt form, as the active ingredient is combined in intimate admixture with a pharmaceutically acceptable carrier, which carrier may take a wide variety of forms depending on the form of preparation desired for administration.

These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example may be prepared in which the carrier comprises saline solution, glucose solution or a mixture of saline and glucose solution. Injectable suspensions may also be prepared in which case appropriate liquid carriers, suspending agents and the like may be employed. Acid addition salts of (I), due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like; and segregated multiples thereof.

In addition to being antihistaminic, anti-allergic and antiasthmatic agents the compounds of formula (I) are also vasoactive and as a result they can be used in the treatment of patients suffering from vascular diseases, particularly disturbances of the periferal vascular system.

The following examples are intended to illustrate and not to limit the scope of the present invention.

Unless otherwise stated all parts therein are by weight.

EXAMPLE I

A mixture of 10.3 parts of 1-chloro-4-(chloromethyl)-2-nitrobenzene, 25.2 parts of 1-(diphenylmethyl)piperazine and 120 parts of ethanol is stirred and refluxed for 4 hours. The reaction mixture is cooled and evaporated. The residue is taken up in about 100 parts of water and the product is extracted with methylbenzene. The extract is washed with water, dried, filtered and evaporated. The residue is purified by column-chromatography over silica gel using trichloromethane as eluent. The pure fractions are collected and the eluent is evaporated. The residue is crystallized from a mixture of 2,2'-oxybispropane and hexane (1:2 by volume). The product is filtered off, washed with hexane and dried, yielding 19.6 parts of 1-(4-chloro-3-nitrophenylmethyl)-4-(diphenylmethyl)piperazine; mp. 101.6° C.

EXAMPLE II

During 20 hours, gaseous methanamine is bubbled through a stirred and hot (60°-70° C.) mixture of 63.3 parts of 1-(4-chloro-3-nitrophenylmethyl)-4-(diphenylmethyl)piperazine and 450 parts of dimethylsulfoxide. The reaction mixture is cooled and poured onto ice-water. The precipitated product is filtered off, washed with water and taken up in methylbenzene. The latter is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 2,2'-oxybispropane, yielding 30.4 parts of 4-[4-(diphenylmethyl)-1-piperazinylmethyl]N-methyl-2-nitrobenzenamine; mp. 120.6° C.

EXAMPLE III

Following the procedure of Example II and using in place of the methanamine used therein an equivalent amount of an appropriate amine, either in gas-form, when said amine is ethanamine, or in liquid form, when said amine is other than ethanamine, the following compounds are obtained:

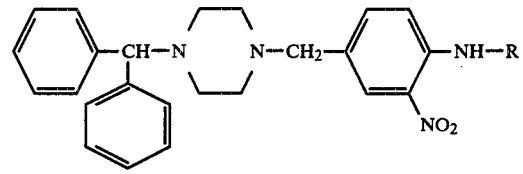

| R | melting point |
|---|---|
| C₂H₅ | 128.2° C. |
| n C₃H₇ | 124.4° C. |
| CH(CH₃)₂ | 119.5° C. |
| n C₄H₉ | 101.4° C. |
| CH₂—CH(CH₃)₂ | 143.2° C. |
| nC₅H₁₁ | 125° C. |
| n C₆H₁₃ | 129.5° C. |
| CH₂—CH₂OH | 123.2° C. |
| ◁ | — (oil) |
| ⬠ | — |
| CH₂—C₆H₅ | 129.5° C. |

EXAMPLE IV

A solution of 5 parts of 4-[4-(diphenylmethyl)-1-piperazinylmethyl]-N-methyl-2-nitrobenzenamine in 80 parts of methanol is hydrogenated at normal pressure and at room temperature with 2 parts of Raney-nickel catalyst. After the calculated amount of hydrogen is taken up, the catalyst is filtered off and the filtrate is evaporated, yielding 4.64 parts of 4-[4-(diphenylmethyl)-1-piperazinylmethyl]-N¹-methyl-1,2-benzenediamine as a residue.

EXAMPLE V

Following the procedure of Example IV and using an equivalent amount of one of the products obtained in Example III as a starting material, the following compounds are obtained as a residue:

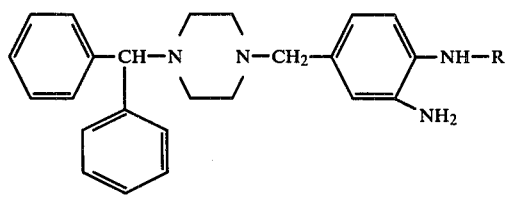

R
C₂H₅
n C₃H₇
CH(CH₃)₂

-continued

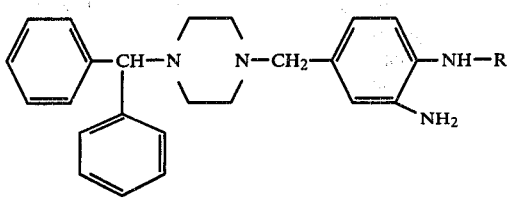

R
n C₄H₉
CH₂—CH(CH₃)₂
n C₅H₁₁
n C₆H₁₃
CH₂—CH₂OH

◁

⬠

CH₂—C₆H₅

EXAMPLE VI

A mixture of 7.1 parts of 4-fluoro-3-nitrobenzoic acid, 9.1 parts of 1-propanamine and 25 parts of dimethyl sulfoxide is stirred for 3 hours at 60° C. The reaction mixture is poured onto 150 parts of water. The precipitated product is filtered off, washed with water and dried, yielding 8.8 parts of 3-nitro-4-(propylamino)benzoic acid; mp. 208° C.

A mixture of 4.5 parts of 3-nitro-4-(propylamino)benzoic acid and 80 parts of methanol is hydrogenated at normal pressure and at room temperature with 2 parts of Raney-nickel catalyst. After the calculated amount of hydrogen is taken up, the catalyst is filtered off, 100 parts of acetic acid are added to the filtrate and the whole is evaporated, yielding 4.5 parts of 3-amino-4-(propylamino)benzoic acid as a residue.

A mixture of 4.5 parts of 3-amino-4-(propylamino)-benzoic acid, 2.6 parts of ethyl ethanecarboximidate hydrochloride and 50 parts of acetic acid is stirred first for 20 minutes at room temperature and further for 10 minutes at reflux. The reaction mixture is evaporated. The residue is crystallized from 2-propanol. The product is filtered off, washed with water and 2-propanol and dried, yielding 1.8 parts of 2-methyl-1-propyl-1H-benzimidazole-5-carboxylic acid; mp. >260° C.

To a stirred mixture of 18 parts of 2-methyl-1-propyl-1H-benzimidazole-5-carboxylic acid and 150 parts of trichloromethane are added dropwise 29.8 parts of thionyl chloride. Upon completion, stirring is continued for 20 minutes at reflux. The reaction mixture is cooled, dried, filtered and evaporated, yielding 22.5 parts of 2-methyl-1-propyl-1H-benzimidazole-5-carbonyl chloride monohydrochloride as a residue.

A solution of 22.5 parts of 2-methyl-1-propyl-1H-benzimidazole-5-carbonyl chloride monohydrochloride in 150 parts of trichloromethane is decomposed with 32 parts of methanol. After stirring for 10 minutes at reflux, the reaction mixture is evaporated. The residue is taken up in water and the whole is alkalized with ammonium hydroxide. The product is extracted twice with 120 parts of dichloromethane. The combined extracts are dried, filtered and evaporated. The solid residue is washed with 2,2'-oxybispropane and dried, yielding 18.8 parts of methyl 2-methyl-1-propyl-1H-benzimidazole-5-carboxylate.

To a stirred solution of 18 parts of sodium dihydrobis(2-methoxyethoxy)aluminate in 22.5 parts of methylbenzene is added dropwise a solution of 11.6 parts of methyl 2-methyl-1-propyl-1H-benzimidazole-5-carboxylate in 45 parts of methylbenzene. Upon completion, stirring at room temperature is continued for 15 minutes. The reaction mixture is decomposed with sodium hydroxide 10 N. The organic phase is separated, dried, filtered and evaporated. The residue is converted into the hydrochloride salt in 2-propanone and 2-propanol. The salt is filtered off and dried, yielding 6.7 parts of 2-methyl-1-propyl-1H-benzimidazole-5-methanol monohydrochloride; mp. +260° C.

A solution of 36 parts of 2-methyl-1-propyl-1H-benzimidazole-5-methanol in 150 parts of trichloromethane is acidified with an excess of gaseous hydrogen chloride. Then there are added dropwise 32 parts of thionyl chloride. Upon completion, the whole is stirred for one hour at room temperature. The reaction mixture is evaporated and the residue is crystallized from 2-propanone. The product is filtered off, washed with 2-propanone and dried, yielding 40.9 parts of 5-(chloromethyl)-2-methyl-1-propyl-1H-benzimidazole monohydrochloride; mp. 180° C.

EXAMPLE VII

A mixture of 8.3 parts of 4-amino-3-nitrobenzaldehyde in 200 parts of methanol is hydrogenated at normal pressure and at room temperature with 5 parts of Raney-nickel catalyst. After a calculated amount of hydrogen is taken up, the catalyst is filtered off and the filtrate is evaporated, yielding 8.5 parts of 3,4-diaminobenzenemethanol as an oily residue.

EXAMPLE VIII

A mixture of 6.9 parts of 3,4-diaminobenzenemethanol, 8.3 parts of ethyl butanimidate hydrochloride and 80 parts of ethanol is stirred first for 2 hours at room temperature and further for 2 hours at reflux. The reaction mixture is evaporated and the residue is stirred in water. The whole is alkalized with ammonium hydroxide and the product is extracted with 4-methyl-2-pentanone. The extract is dried, filtered and evaporated, yielding 6.2 parts of 2-propyl-1H-benzimidazole-5-methanol as a residue.

EXAMPLE IX

Following the procedure of Example VIII and using an equivalent amount of an appropriate iminoester in hydrochloride salt form, the following 1H-benzimidazole-5-methanols are prepared in free base form or in hydrochloride salt form after treatment of the free base with hydrochloric acid in a mixture of ethanol and 2-propanol:

2-methyl-1H-benzimidazole-5-methanol hydrochloride; mp. 200° C.;
2-phenyl-1H-benzimidazole-5-methanol hydrochloride; mp. 220° C.;
2-(1-methylethyl)-1H-benzimidazole-5-methanol; as a residue;
2-ethyl-1H-benzimidazole-5-methanol as a residue;
2-cyclopentyl-1H-benzimidazole-5-methanol as a residue; and
2-cyclopropyl-1H-benzimidazole-5-methanol as a residue.

EXAMPLE X

To 8.5 parts of 3,4-diaminobenzenemethanol are added successively 35 parts of 1,1',1''-[methylidynetris(oxy)]-trisethane and 3 drops of acetic acid. The whole is stirred and refluxed for 2 hours. The reaction mixture is evaporated and the residue is converted into the hydrochloride salt in 2-propanol. The salt is filtered off and washed with a small amount of 2-propanol, yielding, after drying, 7.4 parts of 1H-benzimidazole-5-methanol hydrochloride; mp. 190° C.

EXAMPLE XI

To a stirred mixture of 6.2 parts of 2-propyl-1H-benzimidazole-5-methanol and 38 parts of trichloromethane are added dropwise 40 parts of thionyl chloride. Upon completion, stirring is continued for 15 minutes at reflux temperature. The solvent is evaporated and the residue is dissolved in 80 parts of 2-propanone. The product is allowed to crystallize. It is filtered off and dried, yielding 4.3 parts of 5-(chloromethyl)-2-propyl-1H-benzimidazole monohydrochloride.

EXAMPLE XII

Following the procedure of Example XI, the following 5-(chloromethyl)-1H-benzimidazole hydrochloride salts are derived from the corresponding alcohols:

5-(chloromethyl)-2-ethyl-1H-benzimidazole monohydrochloride;
5-(chloromethyl)-2-(1-methylethyl)-1H-benzimidazole monohydrochloride;
5-(chloromethyl)-2-cyclopentyl-1H-benzimidazole monohydrochloride; and
5-(chloromethyl)-2-cyclopropyl-1H-benzimidazole monohydrochloride.

EXAMPLE XIII

By repeating the procedure of Example XI and using an equivalent amount of an appropriate 1H-benzimidazole-5-methanol or a hydrochloride salt thereof and by carrying out the reaction in the absence of trichloromethane, the following 5-(chloromethyl)-1H-benzimidazole monohydrochlorides are obtained:

5-(chloromethyl)-2-methyl-1H-benzimidazole monohydrochloride; mp. 205° C.;
5-(chloromethyl)-1H-benzimidazole monohydrochloride; mp. 215° C.; and
5-(chloromethyl)-2-phenyl-1H-benzimidazole monohydrochloride; mp. 228° C.

EXAMPLE XIV

A mixture of 4.64 parts of 4-[4-(diphenylmethyl)-1-piperazinylmethyl]-N$^1$-methyl-1,2-benzenediamine, 3.71 parts of methyl N,N'-bis(methoxycarbonyl)carbamimidothioate, 4.32 parts of acetic acid and 150 parts of trichloromethane is stirred and refluxed for 22 hours. The reaction mixture is cooled to room temperature and evaporated. The residue is taken up in about 100 parts of water. The formed precipitate is filtered off and the filtrate is alkalized with ammonium hydroxide. The product is extracted with trichloromethane. The extract is washed with water, dried, filtered and evaporated. The residue is purified by column-chromatography over silica gel using a mixture of trichloromethane and methanol (95:5 by volume) as eluent. The pure fractions are collected and the eluent is evaporated. The residue is crystallized from 2-propanone. The product is filtered off, washed with 2-propanone and with 2,2-oxybispropane, and dried, yielding 2.6 parts of methyl {5-[4-(diphenylmethyl)-1-piperazinylmethyl]-1-methyl-1H-benzimidazol-2-yl} carbamate; mp. 196.5° C.

EXAMPLE XV

A mixture of 4.64 parts of 4-[4-(diphenylmethyl)-1-piperazinylmethyl]-N¹-methyl-1,2-benzenediamine and 1.2 parts of urea is stirred and heated for 1.50 hours at 190° C. The reaction mixture is cooled and dissolved in a mixture of 150 parts of water and 6 parts of a hydrochloric acid solution 10 N. The solution is treated with activated charcoal. The latter is filtered off and the filtrate is alkalized with a sodium hydroxide solution 5 N. The product is extracted three times with dichloromethane. The combined extracts are dried, filtered and evaporated. The solid residue is stirred in 20 parts of ethanol. The product is filtered off and purified by column-chromatography over silica gel using a mixture of trichloromethane and methanol (97.5:2.5 by volume) as eluent. The pure fractions are collected and the eluent is evaporated. The solid residue is treated with 20 parts of ethanol. The product is filtered off, washed with a small amount of ethanol and dried, yielding 1.7 parts of 5-[4-(diphenylmethyl)-1-piperazinylmethyl]-1,3-dihydro-1-methyl-2H-benzimidazol-2-one; mp. 246° C.

EXAMPLE XVI

Following the procedure of Example XV, there is prepared 5-[4-(diphenylmethyl)-1-piperazinylmethyl]-1-ethyl-1,3-dihydro-2H-benzimidazol-2-one; mp. 239.8° C. by the reaction of 4-[4-(diphenylmethyl)-1-piperazinylmethyl]-N¹-ethyl-1,2-benzenediamine with urea.

EXAMPLE XVII

A mixture of 5 parts of 4-[4-(diphenylmethyl)-1-piperazinylmethyl]-N¹-propyl-1,2-benzenediamine, 35 parts of 1,1',1''-[methylidynetris(oxy)]trisethane and 1.5 parts of acetic acid is stirred and refluxed for 2 hours. The reaction mixture is cooled and evaporated. The residue is taken up in 100 parts of water and a hydrochloric acid solution 10 N is added till all solid enters solution. This solution is treated with activated charcoal. The latter is filtered off and the filtrate is alkalized with a sodium hydroxide solution. The product is extracted with dichloromethane. The extract is dried, filtered and evaporated. The residue is purified by column-chromatography over silica gel using a mixture of trichloromethane and methanol (95:5 by volume) as eluent. The pure fractions are collected and the eluent is evaporated. The residue is crystallized from 4-methyl-2-pentanone. The product is filtered off, washed with a small amount of 4-methyl-2-pentanone and with 2,2'-oxybispropane, and dried, yielding 2.2 parts of 5-[4-(diphenylmethyl)-1-piperazinylmethyl]-1-propyl-1H-benzimidazole; mp. 154.8° C.

EXAMPLE XVIII

Following the procedure of Example XVII and using an equivalent amount of an appropriate 4-[4-(diarylmethyl)-1-piperazinylmethyl]-1,2-benzenediamine in place of the 4-[4-(diphenylmethyl)-1-piperazinylmethyl]-N¹-propyl-1,2-benzenediamine used therein, the following compounds are obtained in free base form or in the form of a hydrochloride salt after treatment of the free base with hydrochloric acid in a mixture of ethanol and 2-propanol:

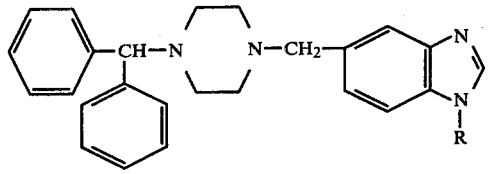

| R | base or salt form | melting point |
|---|---|---|
| CH₃ | base | 179° C. |
| C₂H₅ | base | 164.3° C. |
| CH(CH₃)₂ | base | 133.1° C. |
| n C₄H₉ | base | 164.5° C. |
| CH₂—CH(CH₃)₂ | base | 170° C. |
| n C₅H₁₁ | base | 158.4° C. |
| n C₆H₁₃ | base | 136.2° C. |
| CH₂—CH₂OH | 3 HCl | 229.4° C. |
|  | base | 143.8° C. |
| ◁ |  |  |
| ◁ (cyclopentyl) | base | 143.4° C. |
| CH₂—C₆H₅ | base | 193.5° C. |

EXAMPLE XIX

A mixture of 4.6 parts of 4-[4-(diphenylmethyl)-1-piperazinylmethyl]-N¹-methyl-1,2-benzenediamine, 1.48 parts of ethyl ethanimidate hydrochloride and 80 parts of 2-propanol is gently heated till all solid enters solution. Stirring is continued first for 1 hour at room temperature and further for 3 hours at reflux. The reaction mixture is cooled to room temperature and filtered. The filtrate is evaporated. The residue is taken up in water and a hydrochloric acid solution is added till all solid enters solution. This solution is treated with activated charcoal. The latter is filtered off and the filtrate is alkalized with a sodium hydroxide solution 60%. The product is extracted with dichloromethane. The extract is washed with water, dried, filtered and evaporated. The residue is purified by column-chromatography over silica gel using a mixture of trichloromethane, methanol and ammonium hydroxide (97:2:1 by volume) as eluent. The pure fractions are collected and the eluent is evaporated. The residue is crystallized from 2-propanol. The product is filtered off, washed with 2-propanol and with 2,2'-oxybispropane and dried in vacuo over week-end at 80° C., yielding 2.3 parts of 5-[4-(diphenylmethyl)-1-piperazinylmethyl]-1,2-dimethyl-1H-benzimidazole; mp. 206.2° C.

EXAMPLE XX

Following the procedure of Example XIX, there is prepared 5-[4-(diphenylmethyl)-1-piperazinylmethyl]-1-methyl-2-phenyl-1H-benzimidazole; mp. 189.6° C. by the reaction of 4-[4-(diphenylmethyl)-1-piperazinylmethyl]-N¹-methyl-1,2-benzenediamine with ethyl benzenecarboximidate hydrochloride.

EXAMPLE XXI

A mixture of 4.8 parts of 4-[4-(diphenylmethyl)-1-piperazinylmethyl]-N¹-ethyl-1,2-benzenediamine and 25 parts of acetic acid is stirred at room temperature till all solid enters solution. Then there are added 1.73 parts of ethyl ethanimidate hydrochloride and stirring is continued first for one hour at room temperature and further for one hour at reflux. The reaction mixture is evaporated and the residue is stirred in water. The whole is alkalized with a sodium hydroxide solution and the product is extracted with dichloromethane. The extract is dried, filtered and evaporated. The residue is purified by column-chromatography over silica gel using a mixture of trichloromethane and methanol (98:2 by volume) as eluent. The pure fractions are collected and the eluent is evaporated. The residue is crystallized from 4-methyl-2-pentanone. The product is filtered off and dried, yielding 2.7 parts of 5-[4-(diphenylmethyl)-1-piperazinylmethyl]-1-ethyl-2-methyl-1H-benzimidazole; mp. 152.9° C.

EXAMPLE XXII

Following the procedure of Example XXI and using equivalent amounts of the appropriate starting materials, there are obtained in free base form or in the form of an acid addition salt after treatment of the free base with an appropriate acid compounds of the formula:

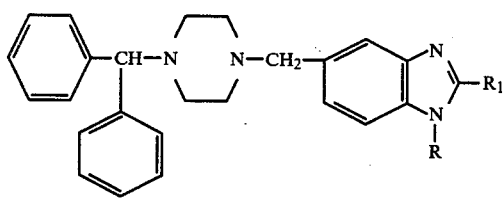

| R | $R^1$ | base or salt form | melting point |
|---|---|---|---|
| n $C_3H_7$ | $CH_3$ | base | 159.2° C. |
| $CH(CH_3)_2$ | $CH_3$ | base | 173.2° C. |
| n $C_4H_9$ | $CH_3$ | base | 146.8° C. |
| $CH_2$—$CH(CH_3)_2$ | $CH_3$ | base | 178.9° C. |
| n $C_5H_{11}$ | $CH_3$ | base | 143.9° C. |
| n $C_6H_{13}$ | $CH_3$ | base | 156.2° C. |
| $CH_2$—$CH_2OH$ | $CH_3$ | base | 212.8° C. |
| ◁ | $CH_3$ | 3½(COOH)$_2$ . H$_2$O | 167.6° C. |
| ⬠ | $CH_3$ | 2(COOH)$_2$ | 156.5° C. |
| $CH_3$ | $C_2H_5$ | base | 165.8° C. |
| $C_2H_5$ | $C_2H_5$ | base | 134.4° C. |
| n $C_3H_7$ | $C_2H_5$ | base | 150.1° C. |
| n $C_4H_9$ | $C_2H_5$ | base | 163.4° C. |
| $CH_2$—$CH(CH_3)_2$ | $C_2_2$ | base | 118.5° ( . $nC_3$) 5 base 128.6° C. |
| n $C_5H_{11}$ | $C_2H_5$ | base | 145.2° C. |
| n $C_6H_{13}$ | $C_2H_5$ | base | 110.2° C. |
| ◁ | $C_2H_5$ | base | 116° C. |
| ⬠ | $C_2H_5$ | base | 172.8° C. |
| $CH_3$ | n $C_3H_7$ | base | 155.3° C. |
| $C_2H_5$ | n $C_3H_{base}$ | | 118.5° C. |
| n $C_3H_7$ | n $C_3H_7$ | base | 138.7° C. |
| $CH(CH_3)_2$ | n $C_3H_7$ | base | 117.2° C. |
| n $C_4H_9$ | n $C_3H_7$ | base | 141.1° C. |
| $CH_2$—$CH(CH_3)_2$ | n $C_3H_7$ | base | 153.2° C. |
| n $C_5H_{11}$ | n $C_3H_7$ | base | 130.7° C. |
| n $C_6H_{13}$ | n $C_3H_7$ | base | 84.5° C. |
| ◁ | n $C_3H_7$ | base | 135.8° C. |
| ⬠ | n $C_3H_7$ | base | 172.2° C. |
| $CH_3$ | $CH(CH_3)_2$ | base | 156.4° C. |
| $C_2H_5$ | $CH(CH_3)_2$ | base | 120.5° C. |
| n $C_3H_7$ | $CH(CH_3)_2$ | base | 102.3° C. |
| $CH(CH_3)_2$ | $CH(CH_3)_2$ | 3(COOH)$_2$ . H$_2$O . ½$C_2H_5OH$ | 142.8° C. |

-continued

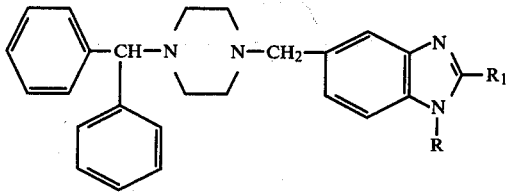

| R | $R^1$ | base or salt form | melting point |
|---|---|---|---|
| n $C_4H_9$ | $CH(CH_3)_2$ | base | 118.3° C. |
| n $C_5H_{11}$ | $CH(CH_3)_2$ | base | 136° C. |
| $CH_2$—$CH(CH_3)_2$ | $CH(CH_3)_2$ | base | 152.3° C. |
| n $C_6H_{13}$ | $CH(CH_3)_2$ | base | 133.6° C. |
| ◁ | $CH(CH_3)_2$ | base | 164° C. |
| ⬠ | $CH(CH_3)_2$ | base | 199.1° C. |
| $CH_3$ | n $C_4H_9$ | . 1½ | 169.8° C. |
| $C_2H_5$ | n $C_4H_9$ | base | 124.8° C. |
| n $C_3H_7$ | n $C_4H_9$ | base | 128° C. |
| $CH(CH_3)_2$ | n $C_4H_9$ | base | 118.1° C. |
| n $C_4H_9$ | n $C_4H_9$ | base | 132.5° C. |
| $CH_2$—$CH(CH_3)_2$ | n $C_4H_9$ | base | 114.7° C. |
| n $C_5H_{11}$ | n $C_4H_9$ | base | 129.8° C. |
| n $C_6H_{13}$ | n $C_4H_9$ | 3½(COOH)$_2$ . ½$H_2O$ | 118.7° C. |
| ◁ | n $C_4H_9$ | base | 152° C. |
| ⬠ | n $C_4H_9$ | base | 176.1° C. |
| $C_2H_5$ | n $C_5H_{11}$ | base | 119° C. |
| n $C_3H_7$ | n $C_5H_{11}$ | base | 115.4° C. |
| $CH_3$ | $CH_2OH$ | base | 195° C. |
| $C_2H_5$ | $CH_2OH$ | base | 176.5° C. |
| $CH_3$ | ◁ | base | 190.9° C. |
| $C_2H_5$ | ◁ | base | 133.5° C. |
| n $C_3H_7$ | ◁ | base | 161.8° C. |
| $CH(CH_3)_2$ | ◁ | 3(COOH)$_2$ . 3$H_2O$ | 144.3° C. |
| n $C_4H_9$ | ◁ | base | 188.3° C. |
| $CH_2$—$CH(CH_3)_2$ | ◁ | base | 146.1° C. |
| n $C_5H_{11}$ | ◁ | base | 167.4° C. |
| n $C_6H_{13}$ | ◁ | base | 106.5° C. |
| ◁ | ◁ | base | 111.5° C. |
| ⬠ | ◁ | base | 143.6° C. |
| $CH_3$ | ⬠ | base | 132.9° C. |
| $C_2H_5$ | ⬠ | base | 164.5° C. |
| n $C_3H_7$ | ⬠ | base | 169.6° C. |
| $CH(CH_3)_2$ | ⬠ | base | 148.7° C. |

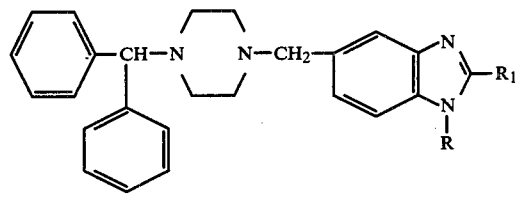

| R | R¹ | base or salt form | melting point |
|---|---|---|---|
| n C₄H₉ |  | base | 138.2° C. |
| CH₂—CH(CH₃)₂ |  | base | 135.8° C. |
| n C₅H₁₁ |  | base | 134.9° C. |
| n C₆H₁₃ |  | base | 126.7° C. |
|  | 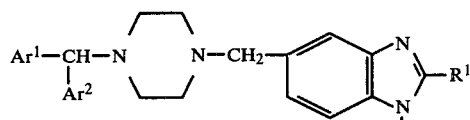 | base | 169.8° C. |

EXAMPLE XXIII

A mixture of 4.05 parts of 1-[(4-fluorophenyl)phenylmethyl]piperazine, 3.9 parts of 5-(chloromethyl)-2-methyl-1-propyl-1H-benzimidazole, 4.8 parts of sodium carbonate and 45 parts of N,N-dimethylformamide is stirred for 3 hours at 50°-60° C. The N,N-dimethylformamide is evaporated and 100 parts of water are added to the residue. The product is extracted twice with methylbenzene. The combined extracts are dried, filtered and evaporated. The residue is converted into the hydrochloride salt in 2-propanol. The salt is filtered off and the free base is liberated in a conventional manner with ammonium hydroxide in water. The product is extracted twice with dichloromethane. The combined extracts are dried, filtered and evaporated. The residue is crystallized from 2,2'-oxybispropane at room temperature, yielding, after drying 4.8 parts of 5-{4-[(4-fluorophenyl)phenylmethyl]-1-piperazinylmethyl}-2-methyl-1-propyl-1H-benzimidazole; mp. 105.1° C.

EXAMPLE XXIV

Following the procedure of Example XXIII and using equivalent amounts of the appropriate starting materials, the following compounds are obtained in free base form or in the form of an acid addition salt after treatment of the free base with an appropriate acid:

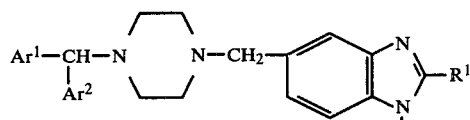

| Ar¹ | Ar² | R | R¹ | salt or base form | melting point |
|---|---|---|---|---|---|
| C₆H₅ | C₆H₅ | H | H | base . H₂O | 129.4° C. |
| C₆H₅ | C₆H₅ | H | CH₃ | 3 HCl . H₂O | 227.7° C. |
| C₆H₅ | 2-pyridinyl | n C₃H₇ | CH₃ | base | 158.8° C. |
| 4-Cl—C₆H₄ | C₆H₅ | n C₃H₇ | CH₃ | base | 106.1° C. |
| 4-F—C₆H₄ | 4-F—C₆H₄ | n C₃H₇ | CH₃ | base | 111.4° C. |
| 4-Cl—C₆H₄ | 2-pyridinyl | n C₃H₇ | CH₃ | 3 HCl . H₂O | 230.1° C. |
| 2-F—C₆H₄ | C₆H₅ | n C₃H₇ | CH₃ | base | 155.4° C. |
| 4-Cl—C₆H₄ | 4-Cl—C₆H₄ | n C₃H₇ | CH₃ | base | 140.6° C. |
| 4-Br—C₆H₄ | C₆H₅ | n C₃H₇ | CH₃ | base | 110.6° C. |
| 4-NO₂—C₆H₄ | C₆H₅ | n C₃H₇ | CH₃ | base | 146.8° C. |
| C₆H₅ | C₆H₅ | H | C₂H₅ | 3 HCl | 232.2° C. |
| C₆H₅ | C₆H₅ | H | n C₃H₇ | 3 HCl . ½ H₂O | 273.5° C. |
| C₆H₅ | C₆H₅ | H | CH(CH₃)₂ | 3 HCl . ½ H₂O | 230.7° C. |
| C₆H₅ | C₆H₅ | H |  | 3(COOH)₂ | 131.2° C. |
| C₆H₅ | C₆H₅ | H |  | 2½ (COOH)₂ | 177.7° C. |
| C₆H₅ | C₆H₅ | H | C₆H₅ | 3 HCl . H₂O | 242.3° C. |
| 3-pyridinyl | C₆H₅ | n C₃H₇ | CH₃ | base | 134.5° C. |

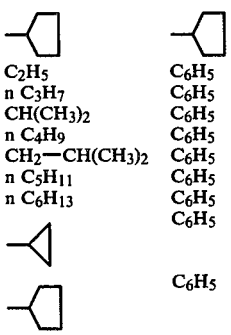

| | | | | |
|---|---|---|---|---|
| | | | base | 192.7° C. |
| C₂H₅ | C₆H₅ | | base | 187.5° C. |
| n C₃H₇ | C₆H₅ | | base | 137.5° C. |
| CH(CH₃)₂ | C₆H₅ | | base . ½H₂O | 215.3° C. |
| n C₄H₉ | C₆H₅ | | base | 122.7° C. |
| CH₂—CH(CH₃)₂ | C₆H₅ | | base | 143.8° C. |
| n C₅H₁₁ | C₆H₅ | | base | 120.1°C. |
| n C₆H₁₃ | C₆H₅ | | base | 117.3° C. |
| | C₆H₅ | | base | 140.8° C. |
| | C₆H₅ | | base | 189.3° C. |

EXAMPLE XXV

To a stirred solution of 4 parts of sodium hydroxide in 50 parts of water are added 4.7 parts of methyl {5-[4-(diphenylmethyl)-1-piperazinylmethyl]-1-methyl-1H-benzimidazol-2-yl]carbamate. The whole is stirred and refluxed for 3.50 hours. The reaction mixture is cooled and allowed to stand overnight. It is acidified with a hydrochloric acid solution 10 N. The precipitated product is filtered off, washed with water and boiled in ethanol. After cooling, the product is filtered off, washed with ethanol and with 2,2'-oxybispropane and dried, yielding 2.5 parts of 5-[4-(diphenylmethyl)-1-piperazinylmethyl]-1-methyl-1H-benzimidazol-2-amine; mp. 267.5° C.

EXAMPLE XXVI

A mixture of 4.1 parts of 5-[4-(diphenylmethyl)-1-piperazinylmethyl]-1-ethyl-1H-benzimidazole, 1.2 parts of sodium amide and 20 parts of N,N-dimethylbenzenamine is stirred and heated slowly to 135° C. Stirring at 135° C. is continued for 3 hours. The reaction mixture is cooled and poured onto water. The product is extracted with trichloromethane. The extract is dried, filtered and evaporated. The residue is purified by column-chromatography over silica gel using a mixture of trichloromethane and methanol (95:5 by volume) and a small amount of ammonium hydroxide as eluent. The pure fractions are collected and the eluent is evaporated. The residue is crystallized from methylbenzene. The product is filtered off and dried, yielding 1.5 parts of 5-[4-(diphenylmethyl)-1-piperazinylmethyl]-1-ethyl-1H-benzimidazol-2-amine; mp. 214.3° C.

EXAMPLE XXVII

To a stirred mixture of 4.1 parts of 5-[4-(diphenylmethyl)-1-piperazinylmethyl]-1-methyl-1H-benzimidazol-2-amine and 25 parts of pyridine are added dropwise 0.79 parts of acetyl chloride while cooling at 0°–5° C. Upon completion, stirring is continued for one hour at 80° C. The reaction mixture is cooled to room temperature, poured onto ice-water and alkalized with ammonium hydroxide. The product is extracted with methylbenzene. The extract is washed with water, dried, filtered and evaporated. The residue is purified by column-chromatography over silica gel using a mixture of trichloromethane and methanol (95:5 by volume) as eluent. The pure fractions are collected and the eluent is evaporated. The residue is crystallized from 2-propanol. The product is filtered off, washed with 2-propanol and 2,2'-oxybispropane, and dried, yielding 3 parts of N-{5-[4-(diphenylmethyl)-1-piperazinylmethyl]-1-methyl-1H-benzimidazol-2-yl}acetamide; mp. 202.5° C.

EXAMPLE XXVIII

Following the procedure of Example XXVII, there is prepared N-{5-[4-(diphenylmethyl)-1-piperazinylmethyl]-1-ethyl-1H-benzimidazol-2-yl}acetamide; mp. 125.7° C. by the reaction of 5-[4-(diphenylmethyl)-1-piperazinylmethyl]-1-ethyl-1H-benzimidazol-2-amine with acetyl chloride.

EXAMPLE XXIX

Following the procedure of Example I and using an equivalent amount of the appropriate starting materials there are prepared:
1-(4-chloro-3-nitrophenylmethyl)4-[(4-fluorophenyl)phenylmethyl]-piperazine; mp. 99.5° C.;
1-[bis(4-fluorophenyl)methyl]-4-(4-chloro-3-nitrophenylmethyl)-piperazine; mp. 105.9° C.; and
1-(diphenylmethyl)-4-(4-methoxy-3-nitrophenylmethyl)piperazine dihydrochloride monohydrate; mp. 257° C.

EXAMPLE XXX

A mixture of 13.9 parts of 1-(diphenylmethyl)piperazine, 8.35 parts of 2-bromo-1-(4-chloro-3-nitrohenyl)ethanone and 40 parts of 2-propanone is stirred for 30 minutes at room temperature. The formed precipitate is filtered off and 210 parts of 2,2'-oxybispropane are added to the filtrate. The whole is treated with activated charcoal. The latter is filtered off and an excess of 2-propanol, previously saturated with gaseous hydrogen chloride, is added to the filtrate. The formed hydrochloride salt is filtered off, stirred in 80 parts of 2-propanol, filtered off again and crystallized from ethanol. The product is filtered off and recrystallized from 2-methoxyethanol, yielding 6.4 parts of 1-(4-chloro-3-nitrophenyl)-2-[4-(diphenylmethyl)-1-piperazinyl]ethanone dihydrochloride; mp. 165° C.

EXAMPLE XXXI

To a stirred mixture of 5.2 parts of 1-(4-chloro-3-nitrophenyl)-2-[4-(diphenylmethyl)-1-piperazinyl]ethanone dihydrochloride in 40 parts of methanol are added portionwise 0.76 parts of sodium borohydride. Upon completion, stirring is continued for 30 minutes at room temperature. The reaction mixture is decomposed by the addition of a mixture of 2 parts of acetic acid and 10 parts of water. The solvent is evaporated and 50 parts of water are added to the residue. The whole is alkalized with ammonium hydroxide. The precipitated product is filtered off, washed with water and with a small amount of 2-propanol, and crystallized from ethanol, yielding 4.3 parts (95.1%) of α-(4-chloro-3-nitrophenyl)-4-(diphenylmethyl)-1-piperazineethanol; mp. 163.4° C.

EXAMPLE XXXII

Following the procedure of Example II and using equivalent amounts of the appropirate starting materials there are prepared:
4-{4-[(4-fluorophenyl)phenylmethyl]-1-piperazinylmethyl}-N-methyl-2-nitrobenzenamine; mp. 108.2° C.;
4-{4-[bis(4-fluorophenyl)methyl]-1-piperazinylmethyl}-N-methyl-2-nitrobenzenamine; mp. 128.8° C.;
2-{[4-{4-[(4-fluorophenyl)phenylmethyl]-1-piperazinylmethyl}-2-nitrophenyl]amino}ethanol; mp. 120.6° C.;
3-[{4-[4-(diphenylmethyl)-1-piperazinylmethyl]-2-nitrophenyl}amino]-1-propanol;
4-(diphenylmethyl)-α-[4-(ethylamino)-3-nitrophenyl]-1-piperazineethanol; mp. 138° C.; and
4-(diphenylmethyl)-α-[3-nitro-4-(propylamino)phenyl]-1-piperazineethanol; mp. 117° C.

EXAMPLE XXXIII

A solution of 20.8 parts of 1-(diphenylmethyl)-4-(4-methoxy-3-nitrophenylmethyl)piperazine dihydrochloride in 50 parts of 2-methoxyethanamine is stirred and refluxed overnight. Water is added and the product is extracted with dichloromethane. The extract is dried, filtered and evaporated. The residue is purified twice by columnchromatography over silica gel using a mixture of trichloromethane and methanol (98:2 by volume) as eluent. The pure fractions are collected and the eluent is evaporated, yielding 11.6 parts (51%) of 4-[4-(diphenylmethyl)-1-piperazinylmethyl]-N-(2-methoxyethyl)-2-nitrobenzenamine; mp. 97.2° C.

EXAMPLE XXXIV

Following the procedure of Example IV and using equivalent amounts of the appropriate starting materials there are prepared:
4-{4-[(4-fluorophenyl)phenylmethyl]-1-piperazinylmethyl}-$N^1$-methyl-1,2-benzenediamine as a residue;
4-{4-[bis(4-fluorophenyl)methyl]-1-piperazinylmethyl}-$N^1$-methyl-1,2-benzenediamine as a residue;
2-{[2-amino-4-{4-[(4-fluorophenyl)phenylmethyl]-1-piperazinylmethyl}phenyl]amino}ethanol as a residue;
3-[{2-amino-4-[4-(diphenylmethyl)-1-piperazinylmethyl]-phenyl}amino]-1-propanol as a residue;

4-[4-(diphenylmethyl)-1-piperazinylmethyl]-N¹-(2-methoxyethyl)-1,2-benzenediamine as a residue;

α-[3-amino-4-(ethylamino)phenyl]-4-(diphenylmethyl)-1-piperazineethanol as an oily residue; and α-[3-amino-4-(propylamino)phenyl]-4-(diphenylmethyl)-1-piperazineethanol as an oily residue.

EXAMPLE XXXV

Following the procedure of Example XXI and using therein as starting materials respectively an appropriate α-[4-(alkylamino)-3-aminophenyl]-4-(diphenylmethyl)-1-piperazineethanol and an appropriate ethyl alkanimidate hydrochloride, there are prepared:

α-[4-(diphenylmethyl)-1-piperazinylmethyl]-1-ethyl-2-methyl-1H-benzimidazole-5-methanol; mp. 174.6° C.;

α-[4-(diphenylmethyl)-1-piperazinylmethyl]-2-methyl-1-propyl-1H-benzimidazole-5-methanol; mp. 146.6° C.;

α-[4-(diphenylmethyl)-1-piperazinylmethyl]-2-ethyl-1-propyl-1H-benzimidazole-5-methanol as an oily residue; and α-[4-(diphenylmethyl)-1-piperazinylmethyl]-1,2-dipropyl-1H-benzimidazole-5-methanol trihydrochloride; mp. 235°–240° C.

EXAMPLE XXXVI

To a stirred mixture of 10.3 parts of α-[4-(diphenylmethyl)-1-piperazinylmethyl]-1-ethyl-2-methyl-1H-benzimidazole-5-methanol trihydrochloride in 75 parts of trichloromethane are added dropwise 4.3 parts of thionyl chloride at room temperature. Upon completion, stirring is continued for 30 minutes at reflux temperature After cooling, the precipitated product is filtered off, washed with trichloromethane and with 2,2'-oxybispropane, and dried, yielding 9 parts (85.8%) of 5-{1-chloro-2-[4-(diphenylmethyl)-1-piperazinyl]-ethyl}1-ethyl-2-methyl-1H-benzimidazole trihydrochloride.

EXAMPLE XXXVII

Following the procedure of Example XXXVI and using equivalent amounts of the appropriate starting materials there are also prepared:

5-{1-chloro-2-[4-(diphenylmethyl)-1-piperazinyl]ethyl}-2-methyl-1-propyl-1H-benzimidazole trihydrochloride; mp. 170°–180° C. (dec.);

5-{1-chloro-2-[4-(diphenylmethyl)-1-piperazinyl]ethyl}-2-ethyl-1-propyl-1H-benzimidazole trihydrochloride; mp. 180° C.; and 5-{1-chloro-2-[4-(diphenylmethyl)-1-piperazinyl]ethyl}-1,2-dipropyl-1H-benzimidazole trihydrochloride.

EXAMPLE XXXVIII

Following the procedure of Example XI, the following 5-chloromethyl-1H-benzimidazole hydrochloride salts are derived from the corresponding alcohols:

5-(chloromethyl)-1,2-dimethyl-1H-benzimidazole monohydrochloride; mp. 204° C.; and 5-(chloromethyl)-1-ethyl-2-methyl-1H-benzimidazole monohydrochloride.

EXAMPLE XXXIX

Following the procedure of steps 3 to 7 of Example VI there is prepared 5-(chloromethyl)-1-ethyl-2-phenyl-1H-benzimidazole monohydrochloride; mp. 175.9° C., starting from 3-amino-4-(ethylamino)benzoic acid and ethyl benzenecarboximidate hydrochloride.

EXAMPLE XL

Following the procedure of Example VIII there is prepared [5-(hydroxymethyl)-1H-benzimidazol-2-ylmethyl]benzoate as a residue by the reaction of 3,4-diaminobenzenemethanol with [2-(ethoxyimino)ethyl]benzoate hydrochloride.

EXAMPLE XLI

Following the procedure of Example XI there is prepared [5-(chloromethyl)-1H-benzimidazol-2-ylmethyl]benzoate monohydrochloride by the reaction of [5-(hydroxymethyl)-1H-benzimidazol-2-ylmethyl]benzoate with thionyl chloride.

EXAMPLE XLII

Following the procedure of Example XIV and using equivalent amounts of the appropriate starting materials the following (1H-benzimidazol-2-yl)carbamates are prepared:

methyl[5-{4-[(4-fluorophenyl)phenylmethyl]-1-piperazinylmethyl}-1-methyl-1H-benzimidazol-2-yl]carbamate; mp. 191.2° C.;

methyl[5-{4-[bis(4-fluorophenyl)methyl]-1-piperazinylmethyl}-1-methyl-1H-benzimidazol-2-yl]carbamate monohydrate; mp. 156.4° C.; and methyl{5-[4-(diphenylmethyl)-1-piperazinylmethyl]-1-propyl-1H-benzimidazol-2-yl}carbamate; mp. 139.5° C.

EXAMPLE XLIII

Following the procedure of Example XVII and using an equivalent amount of an appropriate benzenediamine as a starting material there are prepared:

5-{4-[(4-fluorophenyl)phenylmethyl]-1-piperazinylmethyl}-1H-benzimidazole-1-ethanol hemihydrate; mp. 135.5° C.; and 5-[4-(diphenylmethyl)-1-piperazinylmethyl]-1H-benzimidazole-1-propanol; mp. 130.9° C.

EXAMPLE XLIV

A solution of 2.8 parts of 4-[4-(diphenylmethyl)-1-piperazinylmethyl]-N¹-(2-methoxyethyl)-1,2-benzenediamine, 20 parts of trimethoxymethane and 0.39 parts of acetic acid is stirred and refluxed for 1.50 hours. The reaction mixture is evaporated and the residue is dissolved in a diluted hydrochloric acid solution. The free base is liberated in the conventional manner with ammonium hydroxide and extracted with dichloromethane. The extract is dried, filtered and evaporated. The residue is washed with 2,2'-oxybispropane and dried, yielding 2 parts (70%) of 5-[4-(diphenylmethyl)-1-piperazinylmethyl]-1-(2-methoxyethyl)-1H-benzimidazole; mp. 161.7° C.

EXAMPLE XLV

Following the procedure of Example XXI and using equivalent amounts of the appropriate starting materials the following compounds are prepared:

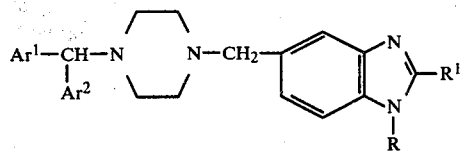

| Ar¹ | Ar² | R | R¹ | melting point |
|---|---|---|---|---|
| C₆H₅ | C₆H₅ | CH₂—CH₂—CH₂OH | CH₃ | 191.2° C. |
| C₆H₅ | C₆H₅ | CH₂—CH₂OH | CH₂—CH₃ | 164.9° C. |
| C₆H₅ | C₆H₅ | CH₂—CH₂OH | CH₂—CH₂—CH₃ | 166.8° C. |
| C₆H₅ | C₆H₅ | CH₂—CH₂OH | CH(CH₃)₂ | 171.6° C. |
| C₆H₅ | C₆H₅ | CH₂—CH₂OH | (CH₂)₄CH₃ | 142.8° C. |
| C₆H₅ | C₆H₅ | CH₂—CH₂OH | ◁ (cyclopropyl) | 177.1° C. |
| C₆H₅ | C₆H₅ | CH₂—CH₂OH | ◁ (cyclobutyl) | 206° C. |
| C₆H₅ | C₆H₅ | CH₂—CH₂—OH | CH₂—C₆H₅ | 210.7° C. |
| C₆H₅ | C₆H₅ | CH₂—CH₂—CH₃ | CH₂—C₆H₅ | 137.5° C. |
| C₆H₅ | C₆H₅ | CH₂—CH₂OH | C₆H₅ | 153.8° C. |
| C₆H₅ | C₆H₅ | CH₂—CH₂—CH₂OH | C₆H₅ | 183° C. |
| 4-F—C₆H₄ | 4-F—C₆H₄ | CH₃ | C₆H₅ | 166.3° C. |
| C₆H₅ | 4-F—C₆H₄ | CH₃ | C₆H₅ | 157.6° C. |
| C₆H₅ | C₆H₅ | CH₃ | 4-F—C₆H₄ | 187.7° C. |
| C₆H₅ | C₆H₅ | CH₃ | 3-CH₃—C₆H₄ | 150.8° C. |
| C₆H₅ | C₆H₅ | CH₃ | 4-OCH₃—C₆H₄ | 202° C. |
| C₆H₅ | C₆H₅ | CH₃ | 4-CH₃—C₆H₄ | 187° C. |
| C₆H₅ | C₆H₅ | CH₂—CH₂—O—CH₃ | C₆H₅ | 172.3° C. |
| C₆H₅ | C₆H₅ | CH₂—CH₂—CH₃ | CH₂OH | 161.8° C. |
| C₆H₅ | C₆H₅ | CH(CH₃)₂ | CH₂OH | 148.5°–149° C. |
| C₆H₅ | C₆H₅ | (CH₂)₃—CH₃ | CH₂OH | 150.8° C. |
| C₆H₅ | C₆H₅ | CH₂—CH(CH₃)₂ | CH₂OH | 182.6° C. |
| C₆H₅ | C₆H₅ | (CH₂)₄—CH₃ | CH₂OH | 121.2°–122.8° C. |
| C₆H₅ | C₆H₅ | (CH₂)₅—CH₃ | CH₂OH | 116.8° C. |
| C₆H₅ | C₆H₅ | ◁ (cyclopropyl) | CH₂OH | 166.3° C. |
| C₆H₅ | C₆H₅ | ◁ (cyclobutyl) | CH₂OH | 159.2°–162.8° C. |
| C₆H₅ | C₆H₅ | CH₂—CH₂OH | CH₂OH | 213.2° C. |
| C₆H₅ | C₆H₅ | CH₂—CH₂—CH₂OH | CH₂OH | 184.7° C. |
| 4-F—C₆H₄ | C₆H₅ | CH₃ | CH₂OH | 184.4° C. |
| 4-F—C₆H₄ | 4-F—C₆H₄ | CH₃ | CH₂OH | 168.1° C. |
| C₆H₅ | C₆H₅ | CH₂—CH₂—CH₃ | CH₂—COOCH₂—CH₃ | 135.2° C. |
| C₆H₅ | C₆H₅ | CH₂—CH₂OH | CH₂—COOCH₂—CH₃ | 169.1° C. |
| C₆H₅ | C₆H₅ | CH₂—CH₂OH | 5-Cl-2-thienyl | 164.5° C. |
| C₆H₅ | C₆H₅ | CH₂—CH₂—CH₃ | 5-Cl-2-thienyl | 146.3° C. |
| C₆H₅ | C₆H₅ | CH₂—CH₂OH | CH(CH₃)—COOC₂H₅ | 159° C. |
| C₆H₅ | C₆H₅ | CH₂—CH₂—CH₃ | CH(CH₃)—COOC₂H₅ | 122° C. |

EXAMPLE XLVI

A mixture of 5.6 parts of 3-[{2-amino-4-[4-(diphenylmethyl)-1-piperazinylmethyl]phenyl}amino]-1-propanol, 2.8 parts of ethyl benzenecarboximidate hydrochloride and 50 parts of acetic acid is stirred first overnight at room temperature and further for 1 hour at reflux. The solvent is evaporated in vacuo and the residue is stirred in water. The whole is alkalized with ammonium hydroxide and the product is extracted with trichloromethane. The extract is dried, filtered and evaporated. The residue is purified by column-chromatography over silica gel using a mixture of trichloromethane and methanol (98.2 by volume) as eluent. The fractions with the highest Rf-value are collected and the eluent is evaporated. The residue is crystallized from 35 parts of 2,2'-oxybispropane. The product is filtered off and dried, yielding 1.8 parts (24.8%) of [3-{5-[4-(diphenylmethyl)-1-piperazinylmethyl]-2-phenyl-1H-benzimidazol-1-yl}propyl]acetate; mp. 111.5° C.

EXAMPLE XLVII

Following the procedure of Example XLVI there is prepared [3-{5-[4-(diphenylmethyl)-1-piperazinylmethyl]-2-methyl-1H-benzimidazol-1-yl}propyl]acetate; mp. 126.6° C., starting from 3-[{2-amino-4-[4-(diphenylmethyl)-1-piperazinylmethyl]phenyl}-amino]-1-propanol and ethyl ethanimidate hydrochloride.

EXAMPLE XLVIII

A mixture of 12.9 parts of N¹-butyl-4-8 4(diphenylmethyl)-1-piperazinylmethyl]-1,2-benzenediamine, 4.6 parts of ethyl 2-hydroxyethanimidate hydrochloride and 100 parts of acetic acid is stirred overnight at room temperature. The whole is heated to reflux and stirring is continued for 3 hours at reflux temperature. The solvent is evaporated in vacuo and the residue is stirred in water. The free base is liberated in the conventional manner with ammonium hydroxide and extracted with trichloromethane. The extract is dried, filtered and evaporated. The residue is purified by column-chromatography over silica gel using a mixture of trichloromethane and methanol (95:5 by volume) as eluent. The fractions with the highest Rf-value are collected and the eluent is evaporated. The residue is crystallized from 21 parts of 2,2'-oxybispropane. The product is filtered off, washed with 2,2'-oxybispropane and dried, yielding 3.5 parts (22.8%) of {1-butyl-5-[4-(diphenylmethyl)-1-piperazinylmethyl]-1H-benzimidazol-2-ylmethyl}acetate; mp. 151.2° C.

EXAMPLE IL

A mixture of 3.9 parts of 4-[4-(diphenylmethyl)-1-piperazinylmethyl]-$N^1$-methyl-1,2-benzenediamine, 2.5 parts of 4-chlorobenzaldehyde and 18 parts of nitrobenzene is stirred in an oil-bath first for 1 hour at 50° C. and further for 1.50 hours at 120° C. The reaction mixture is cooled and allowed to stand overnight at room temperature. About 100 parts of water are added and the whole is acidified with a hydrochloric acid solution 10 N. The product is extracted with 2,2'-oxybispropane. The aqueous phase is treated with activated charcoal. The latter is filtered off and the filtrate is alkalized with a sodium hydroxide solution 50%. The product is extracted with dichloromethane. The extract is washed with water, dried, filtered and evaporated. The residue is crystallized from 35 parts of 1,1'-oxybisethane. The product is filtered off, washed with 1,1'-oxybisethane and dried, yielding 1.3 parts of 2-(4-chlorophenyl)-5-[4-(diphenylmethyl)-1-piperazinylmethyl]-1-methyl-1H-benzimidazole; mp. 198.3° C.

EXAMPLE L

Following the procedure of Example IL and using equivalent amounts of the appropriate starting materials there are prepared:
2-(2-chlorophenyl)-5-[4-(diphenylmethyl)-1-piperazinylmethyl]-1-methyl-1H-benzimidazole; mp. 216.6° C.;
2-(3-chlorophenyl)-5-[4-(diphenylmethyl)-1-piperazinylmethyl]-1-methyl-1H-benzimidazole; mp. 149.4° C.;
5-[4-(diphenylmethyl)-1-piperazinylmethyl]-1-methyl-2-(2-methylphenyl)-1H-benzimidazole; mp. 200.2° C.;
5-[4-(diphenylmethyl)-1-piperazinylmethyl]-1-methyl-2-(4-pyridinyl)-1H-benzimidazole; mp. 149.6° C.; and
5-[4-(diphenylmethyl)-1-piperazinylmethyl]-2-(2-furanyl)-1-methyl-1H-benzimidazole hemihydrate; mp. 185.8° C.

EXAMPLE LI

A mixture of 1.9 parts of 5-[4-(diphenylmethyl)-1-piperazinylmethyl]-1-methyl-1H-benzimidazole-2-methanol, 1.55 parts of acetic acid anhydride and 45 parts of methylbenzene is stirred and refluxed for 2 hours. The reaction mixture is cooled, washed with a diluted ammonium hydroxide solution and the layers are separated. The organic phase is dried, filtered and evaporated. The residue is crystallized from a mixture of methylbenzene and 2,2'-oxybispropane (20:20 by volume). The product is filtered off and dried, yielding 1.5 parts (74.4%) of {5-[4-(diphenylmethyl)-1-piperazinylmethyl]-1-methyl-1H-benzimidazol-2-ylmethyl}acetate; mp. 201.1° C.

EXAMPLE LII

Following the procedure of Example LI the following acetates are derived from the corresponding alcohols:
{5-[4-(diphenylmethyl)-1-piperazinylmethyl]-1-ethyl-1H-benzimidazol-2-ylmethyl}acetate; mp. 159.9° C.;
{5-[4-(diphenylmethyl)-1-piperazinylmethyl]-1-propyl-1H-benzimidazol-2-ylmethyl}acetate; mp. 138.6° C.;
{5-[4-(diphenylmethyl)-1-piperazinylmethyl]-1-(1-methylethyl)-1H-benzimidazol-2-ylmethyl}acetate; mp. 142.1° C.;
{5-[4-(diphenylmethyl)-1-piperazinylmethyl]-1-(2-methylpropyl)-1H-benzimidazol-2-ylmethyl}acetate; mp. 238.9° C. (dec.);
{5-[4-(diphenylmethyl)-1-piperazinylmethyl]-1-pentyl-1H-benzimidazol-2-ylmethyl}acetate; mp. 148.4°–153.2° C.;
{5-[4-(diphenylmethyl)-1-piperazinylmethyl]-1-hexyl-1H-benzimidazol-2-ylmethyl}acetate; mp. 144.7° C.;
{1-cyclopropyl-5-[4-(diphenylmethyl)-1-piperazinylmethyl]-1H-benzimidazol-2-ylmethyl}acetate; mp. 142.4° C.;
{1-cyclopentyl-5-[4-diphenylmethyl)-1-piperazinylmethyl]-1H-benzimidazol-2-ylmethyl}acetate; mp. 190.2°–193.2° C.;
[2-{5-[4-(diphenylmethyl)-1-piperazinylmethyl]-1H-benzimidazol-1-yl}ethyl]acetate; mp. 152.2° C.;
[2-{5-[4-(diphenylmethyl)-1-piperazinylmethyl]-2-methyl-1H-benzimidazol-1-yl}ethyl]acetate; mp. 158° C.; and
[2-{5-[4-(diphenylmethyl)-1-piperazinylmethyl]-2-phenyl-1H-benzimidazol-1-yl}ethyl]acetate; mp. 141.3° C.

EXAMPLE LIII

A mixture of 2.5 parts of 5-[4-(diphenylmethyl)-1-piperazinylmethyl]-2-(hydroxymethyl)-1H-benzimidazole-1-propanol, 3.1 parts of acetic acid anhydride and 45 parts of methylbenzene is stirred and refluxed for 2 hours. The reaction mixture is cooled, washed with alkaline water and the layers are separated. The organic phase is dried, filtered and evaporated. The residue is crystallized from 35 parts of 2,2'-oxybispropane. The product is filtered off and dried, yielding 1.2 parts (40.8%) of [3-{2-(acetyloxymethyl)-5-[4-(diphenylmethyl)-1-piperazinylmethyl]-1H-benzimidazol-1-yl}-propyl]acetate; mp. 100.8° C.

EXAMPLE LIV

Following the procedure of Example XXIII and using equivalent amounts of the appropriate starting materials, the following compounds are prepared:
1-ethyl-5-{4-[(4-fluorophenyl)phenylmethyl]-1-piperazinylmethyl}-2-methyl-1H-benzimidazole; mp. 129.5° C.;
5-{4-[(4-fluorophenyl)phenylmethyl]-1-piperazinylmethyl}-1,2-dimethyl-1H-benzimidazole; mp. 173.6° C.;
5-{4-[bis(4-fluorophenyl)methyl]-1-piperazinylmethyl}-1-ethyl-2-methyl-1H-benzimidazole; mp. 131.6° C.;
5-{4-[bis(4-fluorophenyl)methyl]-1-piperazinylmethyl}-1,2-dimethyl-1H-benzimidazole; mp. 169.9° C.;
1-ethyl-5-{4-[(4-fluorophenyl)phenylmethyl]-1-piperazinylmethyl}-2-phenyl-1H-benzimidazole; mp. 147.9° C.;
5-{4-[bis(4-fluorophenyl)methyl]-1-piperazinylmethyl}-1-ethyl-2-phenyl-1H-benzimidazole; mp. 129.4° C.;
{5-[4-(diphenylmethyl)-1-piperazinylmethyl]-1H-benzimidazol-2-ylmethyl}benzoate; mp. 167.8° C.;
5-{4-[(2-fluorophenyl)(4-methoxyphenyl)methyl]-1-piperazinylmethyl}-2-methyl-1-propyl-1H-benzimidazole; mp. 112.6° C.;

5-{4-[(4-methoxyphenyl)phenylmethyl]-1-piperazinyl-methyl}-2-methyl-1-propyl-1H-benzimidazole; mp. 109.1° C.; and 5-{4-[(4-chlorophenyl)(2-thienyl)methyl]-1-piperazinyl-methyl}-2-methyl-1-propyl-1H-benzimidazole ethanedioate (1:2); mp. 172.8° C.

EXAMPLES LV

Following the procedure of Example XXV the following amines are derived from the corresponding O-methyl carbamates:

5-{4-[(4-fluorophenyl)phenylmethyl]-1-piperazinylmethyl}-1-methyl-1H-benzimidazol-2-amine; mp. 235.3° C.; and 5-{4-[bis(4-fluorophenyl)methyl]-1-piperazinylmethyl}-1-methyl-1H-benzimidazol-2-amine as a residue.

EXAMPLE LVI

Following the procedure of Example XXVII and using equivalent amounts of the appropriate starting materials the following acetamides are prepared:

N-[5-{4-[(4-fluorophenyl)phenylmethyl]-1-piperazinylmethyl}-1-methyl-1H-benzimidazol-2-yl]acetamide; mp. 175.1° C.; and N-[5-{4-[bis(4-fluorophenyl)methyl]-1-piperazinylmethyl}-1-methyl-1H-benzimidazol-2-yl]-acetamide; mp. 198.5° C.

EXAMPLE LVII

To a stirred mixture of 8.8 parts of {5-[4-(diphenylmethyl)-1-piperazinylmethyl]-1H-benzimidazol-2-ylmethyl}benzoate and 120 parts of methanol are added 13.5 parts of sodium hydroxide solution 50% and the whole is stirred and refluxed for 30 minutes. The reaction mixture is evaporated and the residue is stirred in water. The product is extracted with dichloromethane. The extract is dried, filtered and evaporated. The residue is purified by column-chromatography over silica gel using a mixture of trichloromethane and methanol (90:10 by volume) as eluent. The pure fractions are collected and the eluent is evaporated. The residue is crystallized from 45 parts of methylbenzene. The product is filtered off, washed with 2,2'-oxybispropane and dried, yielding 4 parts (57%) of 5-[4-(diphenylmethyl)-1-piperazinylmethyl]-1H-benzimidazole-2-methanol; mp. 137.1° C.

EXAMPLE LVIII

A mixture of 4.1 parts of 5-[4-(diphenylmethyl)-1-piperazinylmethyl]-1-methyl-1H-benzimidazol-2-amine, 1 part of 1-isocyanatobutane and 180 parts of tetrahydrofuran is stirred and refluxed over week-end. After cooling to room temperature, the reaction mixture is filtered and the filtrate is evaporated. The residue is purified by column-chromatography over silica gel using a mixture of trichloromethane and methanol (95:5 by volume) as eluent. The pure fractions are collected and the eluent is evaporated. The residue is crystallized from ethanol. The product is filtered off, washed with ethanol and with 2,2'-oxybispropane, and dried, yielding 3.4 parts (66.7%) of N-butyl-N'-{5-[4-(diphenylmethyl)-1-piperazinylmethyl]-1-methyl-1H-benzimidazol-2-yl}urea; mp. 195.8° C.

EXAMPLE LIX

Following the procedure of Example LVIII there is prepared N-butyl-N'-{5-[4-(diphenylmethyl)-1-piperazinylmethyl]-1-ethyl-1H-benzimidazol-2-yl}urea; mp. 186.4° C., by the reaction of 5-[4-(diphenylmethyl)-1-piperazinylmethyl]-1-ethyl-1H-benzimidazol-2-amine with 1-isocyanatobutane.

EXAMPLE LX

To a stirred solution of 4.4 parts of 5-[4-(diphenylmethyl)-1-piperazinylmethyl]-2-methyl-1H-benzimidazole-1-ethanol in 25 parts of pyridine are added dropwise 1.3 parts of methanesulfonyl chloride. Upon completion, stirring is continued for 1 hour at room temperature. The pyridine is evaporated and 250 parts of water are added to the residue. The product is extracted three times with methylbenzene. The combined extracts are dried, filtered and evaporated. The residue is stirred in a small amount of 2,2'-oxybispropane. The solid product is filtered off and dried, yielding 4.4 parts (84.8%) of [2-{5-[4-(diphenylmethyl)-1-piperazinylmethyl]-2-methyl-1H-benzimidazol-1-yl}ethyl]methanesulfonate; mp. 162.4° C.

EXAMPLE LXI

A stirred mixture of 5.03 parts of 5-[4-(diphenylmethyl)-1-piperazinylmethyl]-2-phenyl-1H-benzimidazole-1-ethanol and 75 parts of trichloromethane is acidified by the introduction of gaseous hydrogen chloride. Then there are added dropwise 2.4 parts of thionyl chloride at room temperature. Upon completion, stirring is continued for 20 minutes at reflux. The reaction mixture is evaporated. 100 Parts of water are added to the residue and the whole is alkalized with sodium hydrogen carbonate. The product is extracted with dichloromethane. The extract is washed with water, dried, filtered and evaporated. The residue is purified by column-chromatography over silica gel using a mixture of trichloromethane and methanol (95:5 by volume) as eluent. The pure fractions are collected and the eluent is evaporated. The residue is crystallized from methylbenzene. The product is filtered off and dried, yielding 3.1 parts of 1-(2-chloroethyl)-5-[4-(diphenylmethyl)-1-piperazinylmethyl]-2-phenyl-1H-benzimidazole; mp. 173.8°-179.6° C.

EXAMPLE LXII

Following the procedure of Example LXI there is prepared 1-(2-chloroethyl)-5-[4-(diphenylmethyl)-1-piperazinylmethyl]-1H-benzimidazole; mp. 206.3° C., starting from 5-[4-(diphenylmethyl)-1-piperazinylmethyl]-1H-benzimidazole-1-ethanol.

EXAMPLE LXIII

To a stirred solution of 0.127 parts of sodium in 20 parts of methanol are added 0.61 parts of benzenethiol. The mixture is stirred for a few minutes and the methanol is evaporated. The residue is taken up in 18 parts of methylbenzene and the latter is evaporated again. The residue is dissolved in 22.5 parts of N,N-dimethylformamide and 2.6 parts of [2-{5-[4-(diphenylmethyl)-1-piperazinylmethyl]-2-methyl-1H-benzimidazol-1-yl}ethyl] methanesulfonate are added at once. The reaction mixture is stirred for 30 minutes at room temperature. The N,N-dimethylformamide is evaporated and 100 parts of water are added to the residue. The product is extracted twice with dichloromethane. The combined extracts are dried, filtered and evaporated. The residue is crystallized from 2-propanol. The product is filtered off and dried, yielding 2.4 parts (90.1%) of 5-[4-(diphenylmethyl)-1-piperazinylmethyl]-2-methyl-1-[2-(phenylthio)ethyl]-1H-benzimidazole; mp. 170.3° C.

EXAMPLE LXIV

To a stirred sodium methoxide solution, prepared starting from 0.127 parts of sodium and 20 parts of methanol are added 0.61 parts of benzenethiol. After stirring for 10 minutes, the solvent is evaporated. The residue is taken up twice in 18 parts of methylbenzene and the latter is evaporated each time. The residue is taken up in 22.5 parts of N,N-dimethylformamide and 2.6 parts of 1-(2-chloroethyl)-5-[4-(diphenylmethyl)-1-piperazinylmethyl]-2-phenyl-1H-benzimidazole are added. The whole is stirred for 1 hour at room temperature. The reaction mixture is evaporated and water is added to the residue. The product is extracted with methylbenzene. The extract is washed with water, dried, filtered and evaporated. The residue is crystallized from 105 parts of 2,2'-oxybispropane. The product is filtered off, washed with 2,2'-oxybispropane and dried, yielding 1.8 parts (60%) of 5-[4-(diphenylmethyl)-1-piperazinylmethyl]-2-phenyl-1-[2-(phenylthio)ethyl]-1H-benzimidazole; mp. 118°–125° C.

EXAMPLE LXV

Following the procedure of Example LXIV there is prepared 5-[4-(diphenylmethyl)-1-piperazinylmethyl]-1-[2-phenylthio)ethyl]-1H-benzimidazole; mp. 172° C. by the reaction of 1-(2-chloroethyl)-5-[4-(diphenylmethyl)-1-piperazinylmethyl]-1H-benzimidazole with benzenethiol.

EXAMPLE LXVI

To 2 parts of a solution of 2 parts of thiophene in 40 parts of ethanol, are added 9 parts of 5-{1-chloro-2-[4-(diphenylmethyl)-1-piperazinyl]ethyl}-1-ethyl-2-methyl-1H-benzimidazole trihydrochloride and 240 parts of methanol. The whole is hydrogenated at normal pressure and at room temperature with 4 parts of palladium-on-charcoal catalyst 10%. After the calculated amount of hydrogen is taken up, the catalyst is filtered off and the filtrate is evaporated. The residue is taken up in 100 parts of water and the whole is alkalized with ammonium hydroxide. The product is extracted twice with dichloromethane. The combined extracts are dried, filtered and evaporated. The residue is purified by column-chromatography over silica gel using a mixture of trichloromethane and methanol (95:5 by volume) as eluent. The pure fractions are collected and the eluent is evaporated. The residue is crystallized from 2-propanol. The product is filtered off and dried, yielding 2.4 parts (35.5%) of 5-{2-[4-(diphenylmethyl)-1-piperazinyl]ethyl}-1-ethyl-2-methyl-1H-benzimidazole monohydrate; mp. 95°–105° C.

EXAMPLE LXVII

Following the procedure of Example LXVI and using equivalent amounts of the appropriate starting materials there are prepared:

5-{2-[4-(diphenylmethyl)-1-piperazinyl]ethyl}-2-methyl-1-propyl-1H-benzimidazole; mp. 115.6° C.;

5-{2-[4-(diphenylmethyl)-1-piperazinyl]ethyl}-2-ethyl-1-propyl-1H-benzimidazole trihydrochloride; mp. 261.2° C.; and 5-{2-[4-(diphenylmethyl)-1-piperazinyl]ethyl}-1,2-dipropyl-1H-benzimidazole trihydrochloride; mp. 250°–255° C.

EXAMPLE LXVIII

To a stirred mixture of 5.03 parts of 5-[4-(diphenylmethyl)-1-piperazinylmethyl]-2-phenyl-1H-benzimidazole-1-ethanol and 50 parts of pyridine are added dropwise 3 parts of benzoyl chloride at room temperature. Upon completion, stirring at room temperature is continued for 2 hours. The reaction mixture is evaporated and water is added to the residue. The product is extracted with dichloromethane. The extract is washed with water, dried, filtered and evaporated. The residue is crystallized from 20 parts of 2-propanol. The product is filtered off, washed with 2-propanol and with 2,2'-oxybispropane and dried, yielding 4 parts (66.5%) of [2-{5-[4-(diphenylmethyl)-1-piperazinylmethyl]-2-phenyl-1H-benzimidazol-1-yl}ethyl]benzoate; mp. 164.1° C.

EXAMPLE LXIX

Following the procedure of Example LXVIII there is prepared [2-{5-[4-(diphenylmethyl)-1-piperazinylmethyl]-1H-benzimidazol-1-yl}ethyl]benzoate 2-propanolate (2:1); mp. 214.6° C., by the reaction of 5-[4-(diphenylmethyl)-1-piperazinylmethyl]-1H-benzimidazole-1-ethanol with benzoyl chloride.

We claim:

1. A chemical compound selected from the group consisting of a 5-[4-(diarylmethyl)-1-piperazinylalkyl]-benzimidazole derivative having the formula:

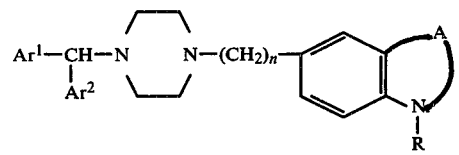

and the pharmaceutically acceptable acid addition salts thereof, wherein:

$Ar^1$ and $Ar^2$ are each independently selected from the group consisting of phenyl, halophenyl, (lower alkyl)phenyl, (lower alkyloxy)phenyl, nitrophenyl, thienyl and pyridinyl;

R is a member selected from the group consisting of hydrogen, lower alkyl, aryl(lower alkyl), hydroxy(lower alkyl), cycloalkyl having from 3 to 6 carbons, (lower alkyl)carbonyloxy(lower alkyl), aroyloxy(lower alkyl), (lower alkyl)sulfonyloxy(lower alkyl), halo(lower alkyl), arylthio(lower alkyl) and (lower alkyl)oxy(lower alkyl) wherein said aryl is selected from the group consisting of phenyl, substituted phenyl, thienyl and pyridinyl, said substituted phenyl being phenyl having from 1 to 2 substituents independently selected from the group consisting of halo, lower alkyl, and lower alkyloxy;

A is a member selected from the group consisting of the bivalent radicals —NH—CO— and —N=C(R$^1$)—, said bivalent radicals being attached to the benzene nucleus with their nitrogen atom, and, said $R^1$ being selected from the group consisting of hydrogen, lower alkyl, aryl(lower alkyl), hydroxy(lower alkyl), cycloalkyl having from 3 to 6 carbons, aryl, amino, (lower alkyl)carbonylamino, (lower alkyl)carbonyloxy(lower alkyl), aroyloxy(lower alkyl), (lower alkyl)oxycarbonylamino, (lower alkyl)aminocarbonylamino, and (lower alkyl)oxycarbonyl(lower alkyl), wherein said aryl is selected from the group consisting of phenyl, substituted phenyl, pyridinyl, furanyl, thienyl and halothienyl, said substituted phenyl having from 1 to 2 substituents independently selected from the group consisting of halo, lower alkyl and lower alkyloxy;

n is an integer of from 1 to 2 inclusive, provided that when said n is 2 then said R is selected from the group consisting of hydrogen, lower alkyl and cycloalkyl, and then said $R^1$ is selected from the group consisting of hydrogen, lower alkyl, cycloalkyl and aryl.

2. A chemical compound selected from the group consisting of 5-{4-[(4-fluorophenyl)phenylmethyl]-1-piperazinylmethyl}-2-methyl-1-propyl-1H-benzimidazole and the pharmaceutically acceptable acid addition salts thereof.

3. A chemical compound selected from the group consisting of N-{5-[4-(diphenylmethyl)-1-piperazinylmethyl]-1-methyl-1H-benzimidazol-2-yl}acetamide and the pharmaceutically acceptable acid additions salts thereof.

4. A chemical compound selected from the group consisting of 5-[4-(diphenylmethyl)-1-piperazinylmethyl]-1-propyl-1H-benzimidazole and the pharmaceutically acceptable acid addition salts thereof.

5. A chemical compound selected from the group consisting of 5-[4-(diphenylmethyl)-1-piperazinylmethyl]-2-methyl-1-propyl-1H-benzimidazole and the pharmaceutically acceptable acid addition salts thereof.

6. A chemical compound selected from the group consisting of 5-[4-(diphenylmethyl)-1-piperazinylmethyl]-1-pentyl-1H-benzimidazole and the pharmaceutically acceptable acid addition salts thereof.

7. A chemical compound selected from the group consisting of 5-[4-(diphenylmethyl)-1-piperazinylmethyl]-1,2-dimethyl-1H-benzimidazole and the pharmaceutically acceptable acid addition salts thereof.

8. A chemical compound selected from the group consisting of 5-[4-(diphenylmethyl)-1-piperazinylmethyl]-1-ethyl-2-methyl-1H-benzimidazole and the pharmaceutically acceptable acid addition salts thereof.

9. A chemical compound selected from the group consisting of 5-[4-(diphenylmethyl)-1-piperazinylmethyl]-1-methyl-1H-benzimidazol-2-amine and the pharmaceutically acceptable acid addition salts thereof.

10. A chemical compound selected from the group consisting of 5-[4-(diphenylmethyl)-1-piperazinylmethyl]-2-(4-fluorophenyl)-1-methyl-1H-benzimidazole and the pharmaceutically acceptable acid addition salts thereof.

11. A chemical compound selected from the group consisting of 5-[4-(diphenylmethyl)-1-piperazinylmethyl]-1-methyl-2-phenyl-1H-benzimidazole and the pharmaceutically acceptable acid addition salts thereof.

12. A chemical compound selected from the group consisting of 5-[4-(diphenylmethyl)-1-piperazinylmethyl]-1-ethyl-2-phenyl-1H-benzimidazole and the pharmaceutically acceptable acid addition salts thereof.

13. A chemical compound selected from the group consisting of 2-butyl-5-[4-(diphenylmethyl)-1-piperazinylmethyl]-1-methyl-1H-benzimidazole and the pharmaceutically acceptable acid addition salts thereof.

14. A pharmaceutical composition comprising an inert carrier material and as an active ingredient an effective antihistaminic, anti-allergic or anti-asthmatic amount of a chemical compound selected from the group consisting of a 5-[4-(diarylmethyl)-1-piperazinylalkyl]-benzimidazole derivative having the formula:

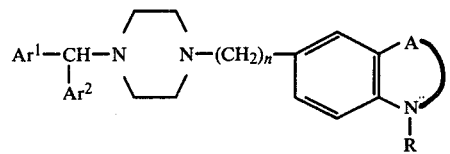

and the pharmaceutically acceptable acid addition salts thereof, wherein:

$Ar^1$ and $Ar^2$ are each independently selected from the group consisting of phenyl, halophenyl, (lower alkyl)phenyl, (lower alkyloxy)phenyl, nitrophenyl, thienyl and pyridinyl;

R is a member selected from the group consisting of hydrogen, lower alkyl, aryl(lower alkyl), hydroxy(lower alkyl), cycloalkyl having from 3 to 6 carbons, (lower alkyl)carbonyloxy(lower alkyl), aroyloxy(lower alkyl), (lower alkyl)sulfonyloxy(lower alkyl), halo(lower alkyl), arylthio(lower alkyl) and (lower alkyl)oxy(lower alkyl) wherein said aryl is selected from the group consisting of phenyl, substituted phenyl, thienyl and pyridinyl, said substituted phenyl being phenyl having from 1 to 2 substituents independently selected from the group consisting of halo, lower alkyl, and lower alkyloxy;

A is a member selected from the group consisting of the bivalent radicals —NH—CO— and —N=C(R$^1$)—, said bivalent radicals being attached to the benzene nucleus with their nitrogen atom, and, said $R^1$ being selected from the group consisting of hydrogen, lower alkyl, aryl(lower alkyl), hydroxy(lower alkyl), cycloalkyl having from 3 to 6 carbons, aryl, amino, (lower alkyl)carbonylamino, (lower alkyl)carbonyloxy(lower alkyl), aroyloxy(lower alkyl), (lower alkyl)oxycarbonylamino, (lower alkyl)aminocarbonylamino, and (lower alkyl)oxycarbonyl(lower alkyl), wherein said aryl is selected from the group consisting of phenyl, substituted phenyl, pyridinyl, furanyl, thienyl and halothienyl, said substituted phenyl having from 1 to 2 substituents independently selected from the group consisting of halo, lower alkyl and lower alkyloxy;

n is an integer of from 1 to 2 inclusive, provided that when said n is 2 then said R is selected from the group consisting of hydrogen, lower alkyl and cycloalkyl, and then said $R^1$ is selected from the group consisting of hydrogen, lower alkyl, cycloalkyl and aryl.

15. A pharmaceutical composition comprising an inert carrier material and as an active ingredient an effective antihistaminic, anti-allergic or anti-asthmatic amount of a chemical compound selected from the group consisting of 5-{4-[(4-fluorophenyl)phenylmethyl]-1-piperazinylmethyl}-2-methyl-1-propyl-1H-benzimidazole and the pharmaceutically acceptable acid addition salts thereof.

16. A pharmaceutical composition comprising an inert carrier material and as an active ingredient an effective antihistaminic, antiallergic or anti-asthmatic amount of a chemical compound selected from the group consisting of 5-[4-(diphenylmethyl)-1-piperazinylmethyl]-1-propyl-1H-benzimidazole and the pharmaceutically acceptable acid addition salts thereof.

17. A pharmaceutical composition comprising an inert carrier material and as an active ingredient an effective antihistaminic, antiallergic or anti-asthmatic amount of a chemical compound selected from the group consisting of 5-[4-(diphenylmethyl)-1-piperazinylmethyl]-2-methyl-1-propyl-1H-benzimidazole and the pharmaceutically acceptable acid addition salts thereof.

18. A pharmeceutical composition comprising a inert carrier material and as an active ingredient an effective antihistaminic, anti-allergic or anti-asthmatic amount of a chemical compound selected from the group consisting of 5-[4-(diphenylmethyl)-1-piperazinylmethyl]-1-pentyl-1H-benzimidazole and the pharmaceutically acceptable acid addition salts thereof.

19. A pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1,2-dimethyl-1H-benzimidazole and the pharmaceutically acceptable acid addition salts thereof.

20. A pharmaceutical composition comprising an inert carrier material and as an active ingredient an effective antihistaminic, antiallergic or anti-asthmatic amount of a chemical compound selected from the group consisting of 5-[4-(diphenylmethyl)-1-piperazinylmethyl]-1-ethyl-2-methyl-1H-benzimidazole and the pharmaceutically acceptable acid addition salts thereof.

21. A pharmaceutical composition comprising an inert carrier material and as an active ingredient an effective antihistaminic, anti-allergic or anti-asthmatic amount of a chemical compound selected from the group consisting of N-{5-[4-(diphenylmethyl)-1-piperazinylmethyl]-1-methyl-1H-benzimidazol-2-yl}acetamide and the pharmaceutically acceptable acid addition salts thereof.

22. A pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-methyl-1H-benzimidazol-2-amine and the pharmaceutically acceptable acid addition salts thereof.

23. A pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-2-(4-fluorophenyl)-1-methyl-1H-benzimidazole and the pharmaceutically acceptable acid addition salts thereof.

24. A pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-methyl-2-phenyl-1H-benzimidazole and the pharmaceutically acceptable acid addition salts thereof.

25. A pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-ethyl-2-phenyl-1H-benzimidazole and the pharmaceutically acceptable acid addition salts thereof.

26. A pharmaceutical composition comprising an inert carrier material and as an active ingredient an effective antihistaminic, anti-allergic or anti-asthmatic amount of a chemical compound selected from the group consisting of 2-butyl-5-[4-(diphenylmethyl)-1-piperazinylmethyl]-1-methyl-1H-benzimidazole and the pharmaceutically acceptable acid addition salts thereof.

27. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of a 5-[4-(diarylmethyl)-1-piperazinylalkyl]-benzimidazole derivative having the formula:

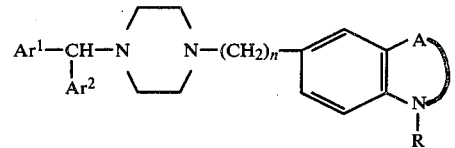

and the pharmaceutically acceptable acid addition salts thereof, wherein:

$Ar^1$ and $Ar^2$ are each independently selected from the group consisting of phenyl, halophenyl, (lower alkyl)phenyl, (lower alkyloxy)phenyl, nitrophenyl, thienyl and pyridinyl;

R is a member selected from the group consisting of hydrogen, lower alkyl, aryl(lower alkyl), hydroxy(lower alkyl), cycloalkyl having from 3 to 6 carbons, (lower alkyl)carbonyloxy(lowr alkyl), aroyloxy(lower alkyl), (lower alkyl)sulfonyloxy(lower alkyl), halo(lower alkyl), arylthio(lower alkyl) and (lower alkyl)oxy(lower alkyl) wherein said aryl is selected from the group consisting of phenyl, substituted phenyl, thienyl and pyridinyl, said substituted phenyl being phenyl having from 1 to 2 substituents independently selected from the group consisting of halo, lower alkyl, and lower alkyloxy;

A is a member selected from the group consisting of the bivalent radicals —NH—CO— and —N=C(R$^1$)—, said bivalent radicals being attached to the benzene nucleus with their nitrogen atom, and, said $R^1$ being selected from the group consisting of hydrogen, lower alkyl, aryl(lower alkyl), hydroxy (lower alkyl), cycloalkyl having from 3 to 6 carbons, aryl, amino, (lower alkyl)carbonylamino, (lower alkyl)carbonyloxy(lower alkyl), aroyloxy(lower alkyl), (lower alkyl)oxycarbonylamino, (lower alkyl)aminocarbonylamino, and (lower alkyl)oxycarbonyl(lower alkyl), wherein said aryl is selected from the group consisting of phenyl, substituted phenyl, pyridinyl, furanyl, thienyl and halothienyl, said substituted phenyl having from 1 to 2 substituents independently selected from the group consisting of halo, lower alkyl and lower alkyloxy;

n is an integer of from 1 to 2 inclusive, provided that when said n is 2 then said R is selected from the group consisting of hydrogen, lower alkyl and cycloalkyl, and then said $R^1$ is selected from the group consisting of hydrogen, lower alkyl, cycloalkyl and aryl.

28. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-{4-[(4-fluorophenyl)-phenylmethyl]-1-piperazinylmethyl}-2-methyl-1-propyl-1H-benzimidazole and the pharmaceutically acceptable acid addition salts thereof.

29. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-propyl-1H-benzimidazole and the pharmaceutically acceptable acid addition salts thereof.

30. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-2-methyl-1-propyl-1H-benzimidazole and the pharmaceutically acceptable acid addition salts thereof.

31. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-pentyl-1H-benzimidazole and the pharmaceutically acceptable acid addition salts thereof.

32. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1,2-dimethyl-1H-benzimidazole and the pharmaceutically acceptable acid addition salts thereof.

33. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-ethyl-2-methyl-1H-benzimidazole and the pharmaceutically acceptable acid addition salts thereof.

34. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of N-{5-[4-(diphenylmethyl)-1-piperazinylmethyl]-1-methyl-1H-benzimidazol-2-yl}acetamide and the pharmaceutically acceptable acid addition salts thereof.

35. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-methyl-1H-benzimidazol-2-amine and the pharmaceutically acceptable acid addition salts thereof.

36. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-2-(4-fluorophenyl)-1-methyl-1H-benzimidazole and the pharmaceutically acceptable acid addition salts thereof.

37. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-methyl-2-phenyl-1H-benzimidazole and the pharmaceutically acceptable acid addition salts thereof.

38. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 5-[4-(diphenylmethyl)-1-piperazinylmethyl]-1-ethyl-2-phenyl-1H-benzimidazole and the pharmaceutically acceptable acid addition salts thereof.

39. A method of inhibiting vasoactive agonist activity in warm-blooded animals which comprises the systemic administration thereto of a pharmaceutical composition comprising an inert carrier material and as an active ingredient an effective antihistaminic, anti-allergic or anti-asthmatic amount of a chemical compound selected from the group consisting of 2-butyl-5-[4-(diphenylmethyl)-1-piperazinylmethyl]-1-methyl-1H-benzimidazole and the pharmaceutically acceptable acid addition salts thereof.

* * * * *